US00RE44823E

(19) United States
(12) Reissued Patent
Parker

(10) Patent Number: US RE44,823 E
(45) **Date of Reissued Patent: *Apr. 1, 2014**

(54) UNIVERSAL MODULAR PULSE OXIMETER PROBE FOR USE WITH REUSABLE AND DISPOSABLE PATIENT ATTACHMENT DEVICES

(75) Inventor: Brent Parker, Gig Harbor, WA (US)
(73) Assignee: Masimo Corporation, Irvine, CA (US)

( * ) Notice: This patent is subject to a terminal disclaimer.
(21) Appl. No.: 13/367,666
(22) Filed: Feb. 7, 2012

Related U.S. Patent Documents

Reissue of:
(64) Patent No.: 6,721,585
Issued: Apr. 13, 2004
Appl. No.: 09/931,273
Filed: Aug. 17, 2001

U.S. Applications:
(60) Division of application No. 12/573,851, filed on Oct. 5, 2009, now Pat. No. Re. 43,169, which is a continuation of application No. 11/404,123, filed on Apr. 13, 2006, now Pat. No. Re. 41,317, which is a continuation-in-part of application No. 09/758,038, filed on Jan. 11, 2001, now Pat. No. 6,684,091, and a continuation-in-part of application No. 09/679,828, filed on Oct. 5, 2000, now Pat. No. 6,519,487, and a continuation-in-part of application No. 09/417,898, filed on Oct. 14, 1999, now Pat. No. 6,343,224, and a continuation-in-part of application No. 09/352,144, filed on Jul. 13, 1999, now Pat. No. 6,321,100, said application No. 09/758,038 is a continuation-in-part of application No. 09/417,898, said application No. 09/679,828 is a continuation-in-part of application No. 09/417,898, and a continuation-in-part of application No. 09/289,647, filed on Apr. 12, 1999, now Pat. No. 6,144,868, said application No. 09/417,898 is a continuation-in-part of application No. 09/289,647.
(60) Provisional application No. 60/104,332, filed on Oct. 15, 1998.
(51) Int. Cl.
*A61B 5/1455* (2006.01)
(52) U.S. Cl.
USPC ..... 600/344; 600/310; 600/340
(58) Field of Classification Search
USPC ..... 600/310, 322, 323, 340, 344
See application file for complete search history.

(56) References Cited

U.S. PATENT DOCUMENTS 3,463,142 A 8/1969 Harte et al.
3,647,299 A 3/1972 Lavallee (Continued)
FOREIGN PATENT DOCUMENTS

AU 745306 6/2000
AU 784021 1/2002

(Continued)
OTHER PUBLICATIONS

Co-pending U.S. Appl. No. 12/917,433, filed Nov. 1, 2010, and pending claims.

(Continued)

*Primary Examiner* — Eric Winakur
(74) *Attorney, Agent, or Firm* — Knobbe Martens Olson & Bear, LLP

(57) ABSTRACT

[A system and method of standardizing modular probe housings so that the standardized probe housings may be incorporated into probes adapted to work with at least one of a multiplicity of manufacturers' oximeters. The probe housings are adapted to matingly engage at least a disposable bandage apparatus and a reusable finger attachment device.] *A sensor system for sensing a physiological parameter of a patient. A reusable probe sensor comprises a first housing element and a second housing element. The first housing element comprises at least one light emitter and the second housing element comprises at least one light detector. The first and second housing elements are movably coupled and configured to receive a disposable sensor shield. A disposable sensor shield comprises a first liner portion having a first aperture and a second liner portion having a second aperture. The first and second liner portions are configured to receive an appendage. The first and second apertures are configured to be aligned to allow light from the at least one light emitter to pass through the first aperture, the appendage, and the second aperture, to the at least one light detector during use. The disposable sensor shield is configured to engage the reusable probe sensor.*

25 Claims, 22 Drawing Sheets

(56) References Cited

U.S. PATENT DOCUMENTS 3,740,570 A 6/1973 Kaelin et al.
3,799,672 A 3/1974 Vurek
4,086,915 A 5/1978 Kofsky et al.
4,169,976 A 10/1979 Cirri
4,182,977 A 1/1980 Stricklin, Jr.
4,308,456 A 12/1981 van der Gaag et al.
4,346,590 A 8/1982 Brown
4,407,290 A 10/1983 Wilber
4,449,821 A 5/1984 Lee
4,480,886 A 11/1984 Bergamin
4,580,867 A 4/1986 Wright et al.
4,621,643 A 11/1986 New, Jr. et al.
4,653,498 A 3/1987 New, Jr. et al.
4,685,464 A 8/1987 Goldberger et al.
4,700,708 A 10/1987 New, Jr. et al.
4,770,179 A 9/1988 New, Jr. et al.
4,830,014 A 5/1989 Goodman et al.
4,848,901 A 7/1989 Hood, Jr.
4,865,038 A 9/1989 Rich et al.
4,877,322 A 10/1989 Hill
4,913,150 A 4/1990 Cheung et al.
4,942,877 A 7/1990 Sakai et al.
4,960,128 A 10/1990 Gordon et al.
4,964,408 A 10/1990 Hink et al.
4,974,591 A 12/1990 Awazu et al.
5,041,187 A 8/1991 Hink et al.
5,058,588 A 10/1991 Kaestle
5,069,213 A 12/1991 Polczynski
5,090,410 A 2/1992 Saper et al.
5,094,240 A 3/1992 Muz
5,113,862 A 5/1992 Mortazavi
5,140,228 A 8/1992 Biegel
5,158,323 A 10/1992 Yamamoto et al.
5,163,438 A 11/1992 Gordon et al.
5,170,786 A 12/1992 Thomas et al.
5,209,230 A 5/1993 Swedlow et al.
5,226,417 A 7/1993 Swedlow et al.
5,246,003 A 9/1993 DeLonzor
5,249,576 A 10/1993 Goldberger et al.
5,267,562 A 12/1993 Ukawa et al.
5,273,041 A 12/1993 Richards et al.
5,279,295 A 1/1994 Martens et al.
5,287,853 A 2/1994 Vester et al.
5,308,919 A 5/1994 Minnich
5,319,355 A 6/1994 Russek
5,337,744 A 8/1994 Branigan
5,339,810 A 8/1994 Ivers et al.
5,341,805 A 8/1994 Stavridi et al.
5,365,937 A 11/1994 Reeves et al.
D353,195 S 12/1994 Savage et al.
D353,196 S 12/1994 Savage et al.
5,377,676 A 1/1995 Vari et al.
5,387,122 A 2/1995 Goldberger et al.
5,397,247 A 3/1995 Aoki et al.
D359,546 S 6/1995 Savage et al.
5,422,632 A 6/1995 Bucholtz et al.
5,431,170 A 7/1995 Mathews
D361,840 S 8/1995 Savage et al.
5,437,275 A 8/1995 Amundsen et al.
D362,063 S 9/1995 Savage et al.
5,452,717 A 9/1995 Branigan et al.
D363,120 S 10/1995 Savage et al.
5,456,252 A 10/1995 Vari et al.
5,460,182 A 10/1995 Goodman et al.
5,479,934 A 1/1996 Imran
5,482,036 A 1/1996 Diab et al.
5,490,505 A 2/1996 Diab et al.
5,494,043 A 2/1996 O'Sullivan et al.
5,507,286 A 4/1996 Solenberger
5,515,169 A 5/1996 Cargill et al.
5,520,177 A 5/1996 Ogawa et al.
5,533,511 A 7/1996 Kaspari et al.
5,561,275 A 10/1996 Savage et al.
5,562,002 A 10/1996 Lalin
5,570,002 A 10/1996 Castleman
5,579,373 A 11/1996 Jang
5,590,649 A 1/1997 Caro et al.
5,602,924 A 2/1997 Durand et al.
5,617,857 A 4/1997 Chader et al.
5,619,992 A 4/1997 Guthrie et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,660,567 A 8/1997 Nierlich et al.
5,664,270 A 9/1997 Bell et al.
5,673,693 A 10/1997 Solenberger
5,678,544 A 10/1997 DeLonzor et al.
5,685,299 A 11/1997 Diab et al.
D393,830 S 4/1998 Tobler et al.
5,743,262 A 4/1998 Lepper, Jr. et al.
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,786,592 A 7/1998 Hök
5,791,347 A 8/1998 Flaherty et al.
5,810,734 A 9/1998 Caro et al.
5,817,008 A 10/1998 Rafert et al.
5,817,010 A 10/1998 Hibl
5,823,950 A 10/1998 Diab et al.
5,830,129 A 11/1998 Baer et al.
5,830,131 A 11/1998 Caro et al.
5,833,618 A 11/1998 Caro et al.
RE36,000 E 12/1998 Swedlow et al.
5,860,919 A 1/1999 Kiani-Azarbayjany et al.
5,879,373 A 3/1999 Roper et al.
5,890,929 A 4/1999 Mills et al.
5,904,654 A 5/1999 Wohltmann et al.
5,910,108 A 6/1999 Solenberger
5,919,133 A 7/1999 Taylor et al.
5,919,134 A 7/1999 Diab
5,934,925 A 8/1999 Tobler et al.
5,940,182 A 8/1999 Lepper, Jr. et al.
5,991,648 A 11/1999 Levin
5,995,855 A 11/1999 Kiani et al.
5,997,343 A 12/1999 Mills et al.
5,999,834 A 12/1999 Wang et al.
6,002,952 A 12/1999 Diab et al.
6,011,986 A 1/2000 Diab et al.
6,014,576 A 1/2000 Raley
6,027,452 A 2/2000 Flaherty et al.
6,036,642 A 3/2000 Diab et al.
6,045,509 A 4/2000 Caro et al.
6,061,584 A 5/2000 Lovejoy et al.
6,067,462 A 5/2000 Diab et al.
6,081,735 A 6/2000 Diab et al.
6,088,607 A 7/2000 Diab et al.
6,110,522 A 8/2000 Lepper, Jr. et al.
6,124,597 A 9/2000 Shehada et al.
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,253,097 B1 6/2001 Aronow et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,285,896 B1 9/2001 Tobler et al.
6,301,493 B1 10/2001 Marro et al.
6,308,089 B1 10/2001 von der Ruhr et al.
6,317,627 B1 11/2001 Ennen et al.
6,321,000 B1 11/2001 King

(56) References Cited

U.S. PATENT DOCUMENTS

| | | | |
|---|---|---|---|
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,381,489 | B1 | 4/2002 | Ashibe |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,484 | B1 | 2/2003 | Lovejoy et al. |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,571,113 | B1 | 5/2003 | Fein et al. |
| 6,580,086 | B1 | 6/2003 | Schulz et al. |
| 6,580,948 | B2 | 6/2003 | Haupert et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,600,940 | B1 | 7/2003 | Fein et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,661,161 | B1 | 12/2003 | Lanzo et al. |
| 6,671,531 | B2 | 12/2003 | Al-Ali et al. |
| 6,671,532 | B1 | 12/2003 | Fudge et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-All |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,839,583 | B1 | 1/2005 | Lewandowski et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,941,162 | B2 | 9/2005 | Fudge et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab et al. |
| 7,215,986 | B2 | 5/2007 | Diab et al. |
| 7,221,971 | B2 | 5/2007 | Diab et al. |
| 7,225,006 | B2 | 5/2007 | Al-Ali et al. |
| 7,225,007 | B2 | 5/2007 | Al-Ali et al. |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali et al. |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al-Ali et al. |
| 7,377,899 | B2 | 5/2008 | Weber et al. |
| 7,383,070 | B2 | 6/2008 | Diab et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |

(56) References Cited

U.S. PATENT DOCUMENTS

| | | | |
|---|---|---|---|
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,526,328 | B2 | 4/2009 | Diab et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,596,398 | B2 | 9/2009 | Al-Ali et al. |
| 7,618,375 | B2 | 11/2009 | Flaherty |
| D606,659 | S | 12/2009 | Kiani et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,706,853 | B2 | 4/2010 | Hacker et al. |
| RE41,317 | E | 5/2010 | Parker |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,224,411 | B2 | 7/2012 | Al-Ali et al. |
| 8,228,181 | B2 | 7/2012 | Al-Ali |
| 8,229,533 | B2 | 7/2012 | Diab et al. |
| 8,255,026 | B1 | 8/2012 | Al-Ali |
| 8,255,028 | B2 | 8/2012 | Al-Ali et al. |
| 8,260,577 | B2 | 9/2012 | Al-Ali et al. |
| 8,274,360 | B2 | 9/2012 | Sampath et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 2001/0029325 | A1 | 10/2001 | Parker |
| 2003/0009092 | A1 | 1/2003 | Parker |
| 2004/0147824 | A1 | 7/2004 | Diab et al. |
| 2005/0245797 | A1 | 11/2005 | Al-Ali et al. |
| 2007/0123763 | A1 | 5/2007 | Al-Ali et al. |
| 2007/0219437 | A1 | 9/2007 | Schurman et al. |
| 2007/0244378 | A1 | 10/2007 | Al-Ali et al. |
| 2008/0009691 | A1 | 1/2008 | Parker |
| 2008/0262324 | A1 | 10/2008 | Van Der Voort et al. |

FOREIGN PATENT DOCUMENTS

| | | |
|---|---|---|
| CA | 2 346 639 | 4/2000 |
| CA | 2 366 493 | 7/2002 |
| EP | 0 019 278 | 11/1980 |
| EP | 019 478 | 11/1980 |
| EP | 0 104 772 | 4/1984 |
| EP | 0 313 238 | 4/1989 |
| EP | 0 745 348 | 12/1996 |
| EP | 1 222 894 | 7/2002 |
| EP | 1 121 049 | 7/2003 |
| EP | 1 683 478 | 11/2007 |
| JP | 59-141932 | 8/1984 |
| JP | 63-192422 | 8/1988 |
| JP | 2-189132 | 7/1990 |
| JP | 4-15045 | 1/1992 |
| JP | A 04-250140 | 9/1992 |
| JP | 5-200017 | 8/1993 |
| JP | 5275746 | 10/1993 |
| JP | 60-34432 | 2/1994 |
| JP | A 06-237013 | 8/1994 |
| JP | 9-504461 | 5/1997 |
| JP | 9-506786 | 7/1997 |
| JP | 11-508691 | 7/1999 |
| JP | 3981271 | 9/2007 |
| JP | 4614537 | 10/2010 |
| WO | WO 88/10462 | 12/1988 |
| WO | WO 92/21281 | 12/1992 |
| WO | WO 99/53831 | 10/1999 |
| WO | WO 00/21433 | 4/2000 |
| WO | WO 00/42911 | 7/2000 |
| WO | WO 01/03574 | 1/2001 |
| WO | WO 01-41634 | 6/2001 |
| WO | WO 02/089664 | 11/2002 |

OTHER PUBLICATIONS

Office Action and translation thereto, received in corresponding Japanese Patent Application No. 2000-575417, mailed Feb. 23, 2010, 6 pages.

PCT International Search Report and Written Opinion, Application No. PCT/US2006/046176, Application Date Nov. 29, 2006 in 10 pages.

de Kock, J.P., et al., "The Effect of Varying LED Intensity on Pulse Oximeter Accuracy," Journal of Medical Engineering & Technology, vol. 15, No. 3.

Reynolds, K.J., et al., "Temperature Dependence of LED and Its Theoretical Effect on Pulse Oximetry," British Journal & Anesthesia, 1991, vol. 67, pp. 638-643.

(56) References Cited

OTHER PUBLICATIONS

Schmitt, Joseph M., "Simple Photon Diffusion Analysis of the Effects of Multiple Scattering on Pulse Oximetry," IEEE Transactions on Biomedical Engineering, vol. 38, No. 12, Dec. 1991, pp. 1194-1203.

Copending U.S. Appl. No. 13/710,287, filed Dec. 10, 2012, and pending claims.

Copending U.S. Appl. No. 13/465,952, filed May 7, 2012, and pending claims.

FIG. 1
NEW
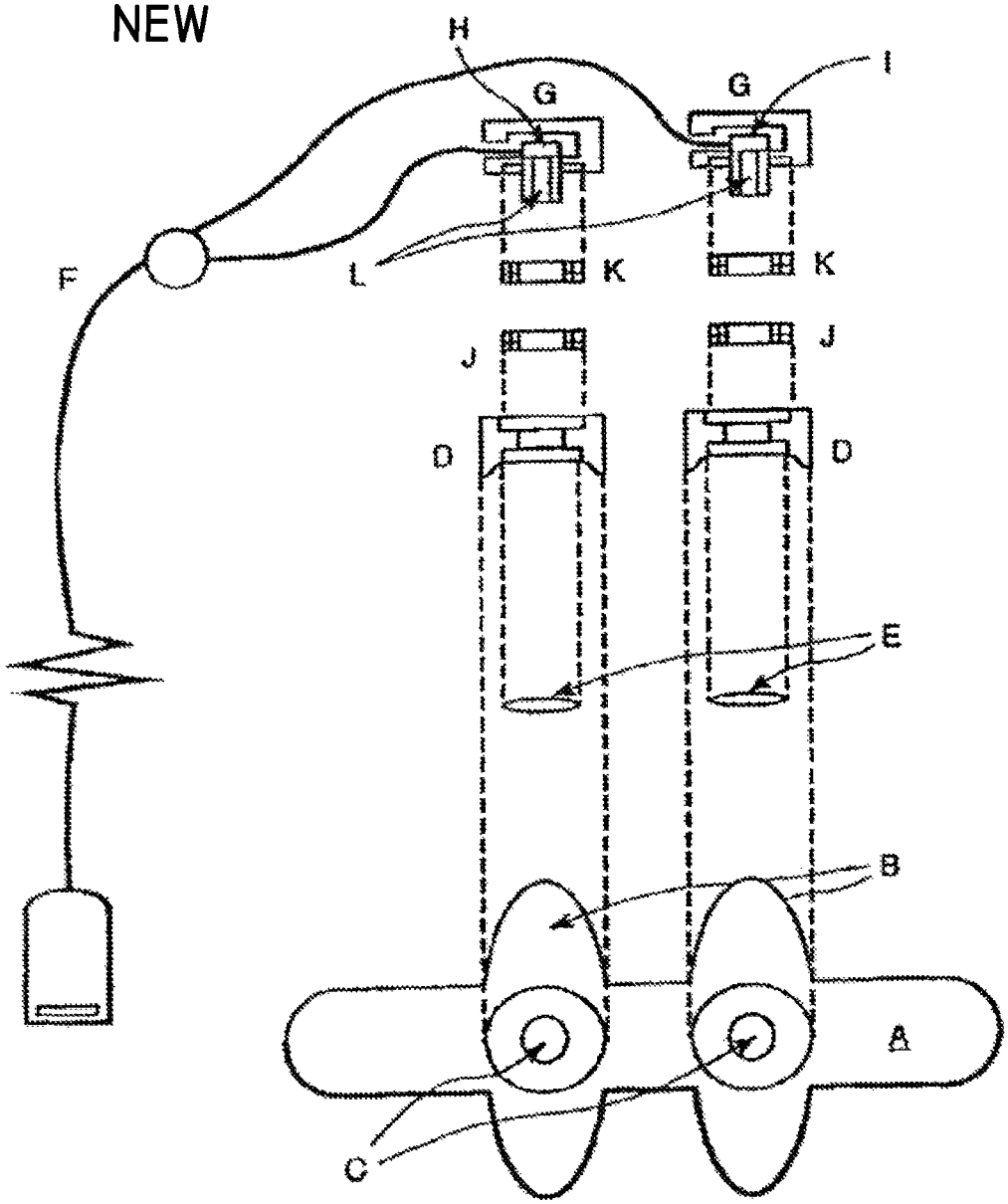

FIG. 2
NEW
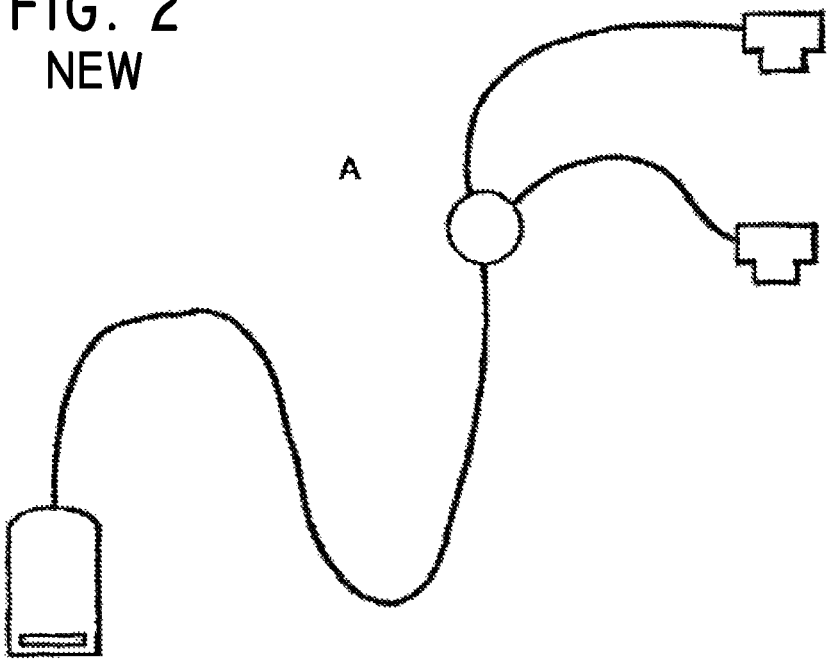
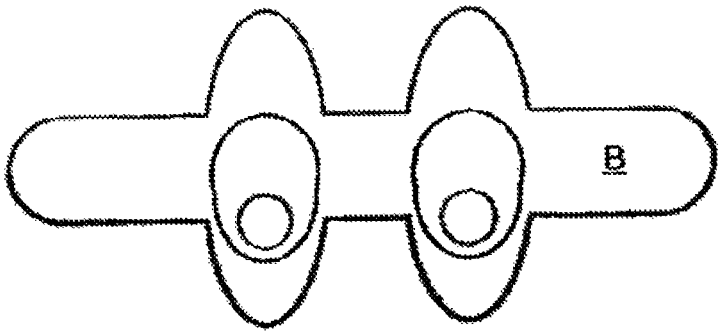

FIG. 3
NEW
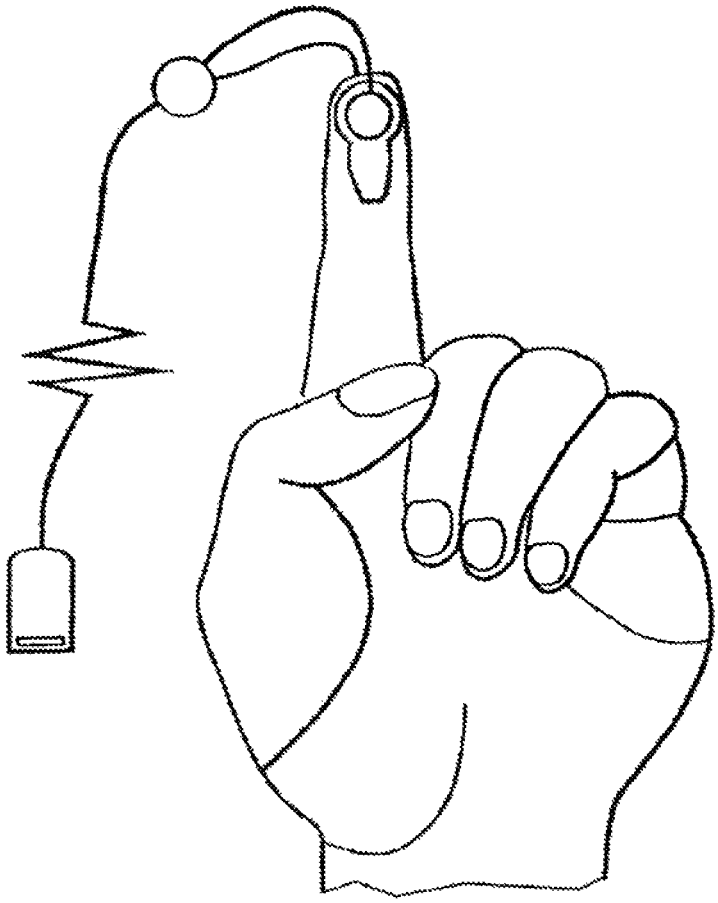

FIG. 4
NEW
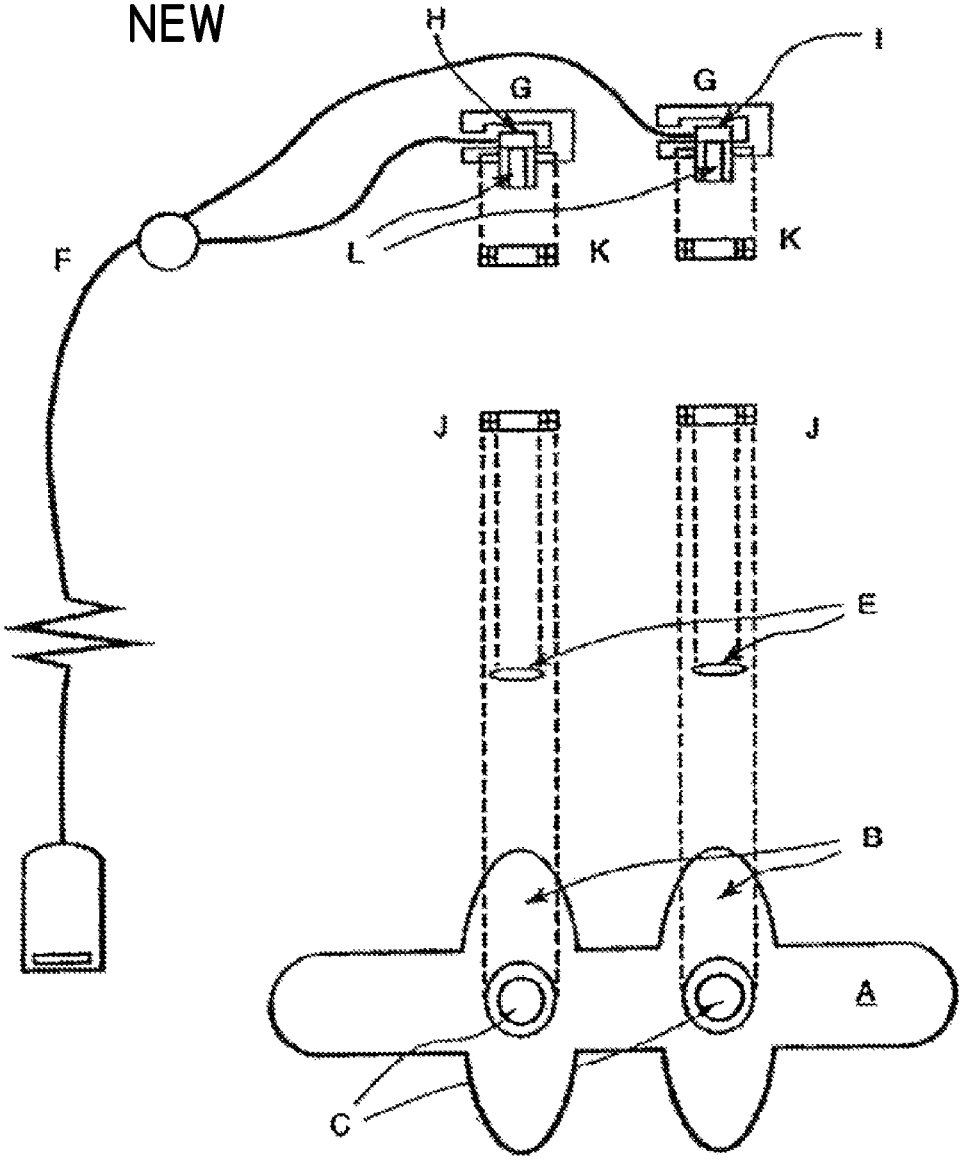

FIG. 5
NEW
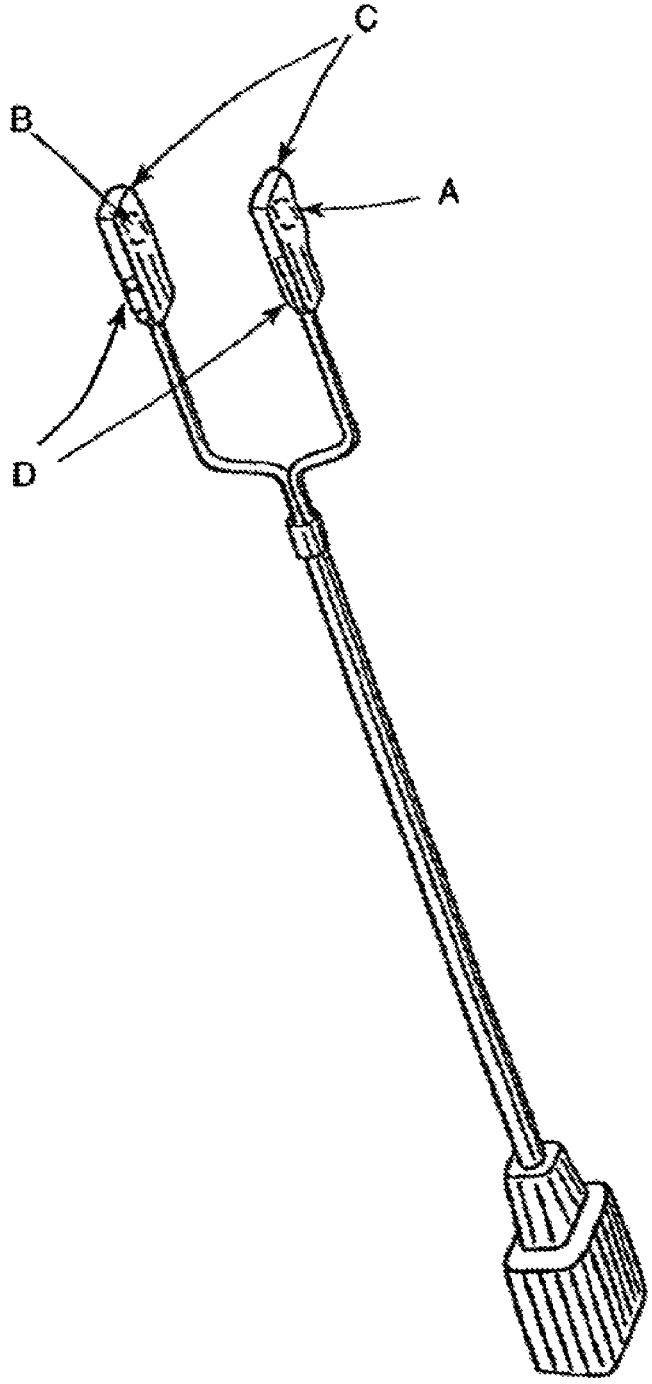

FIG. 6
NEW
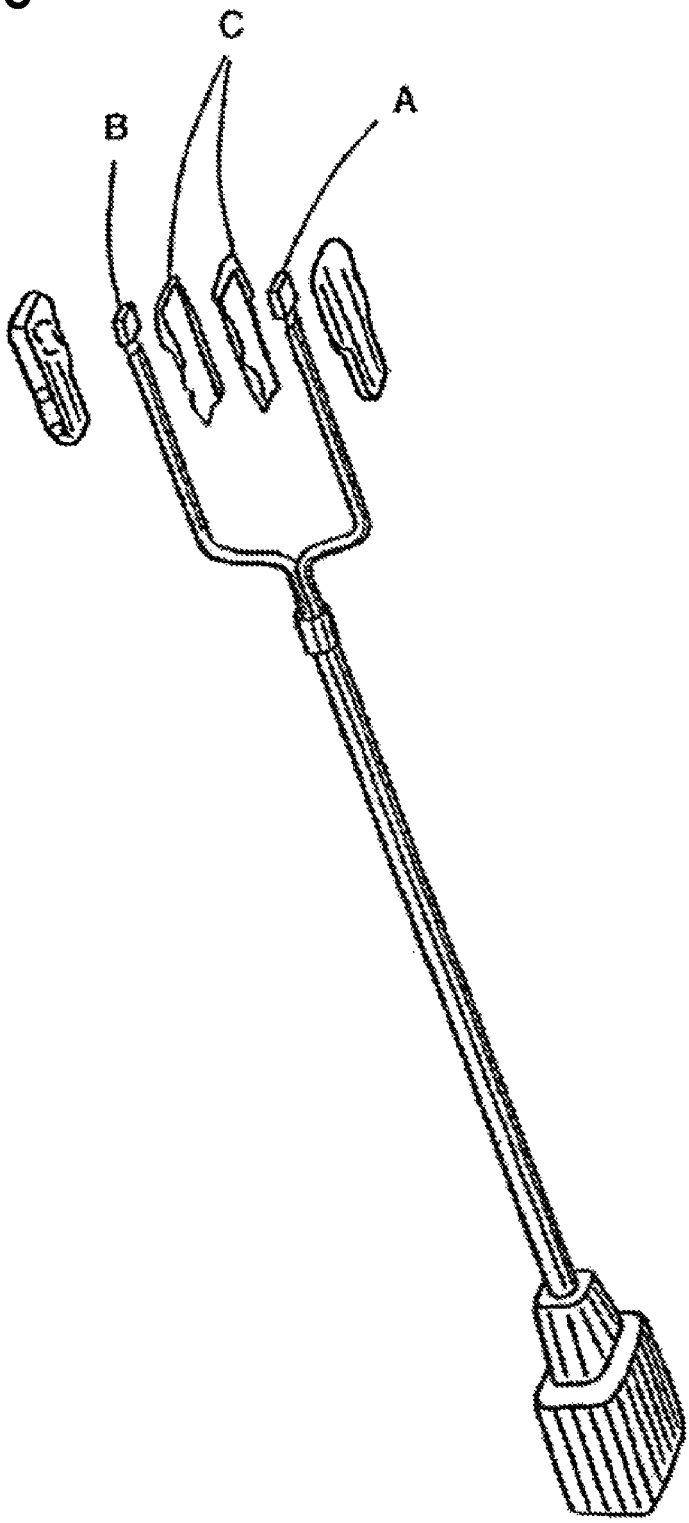

FIG. 7
NEW
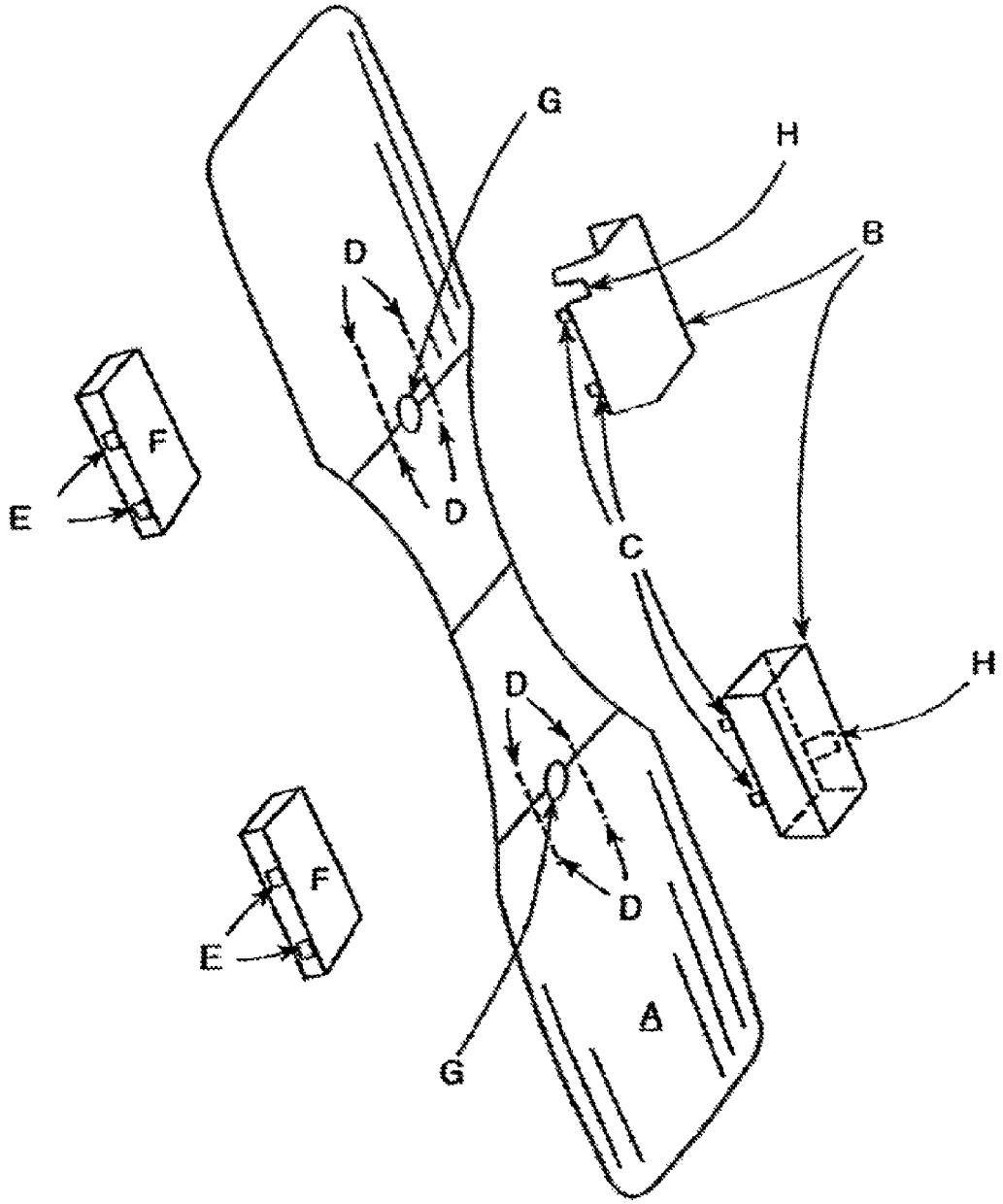

FIG. 8
NEW
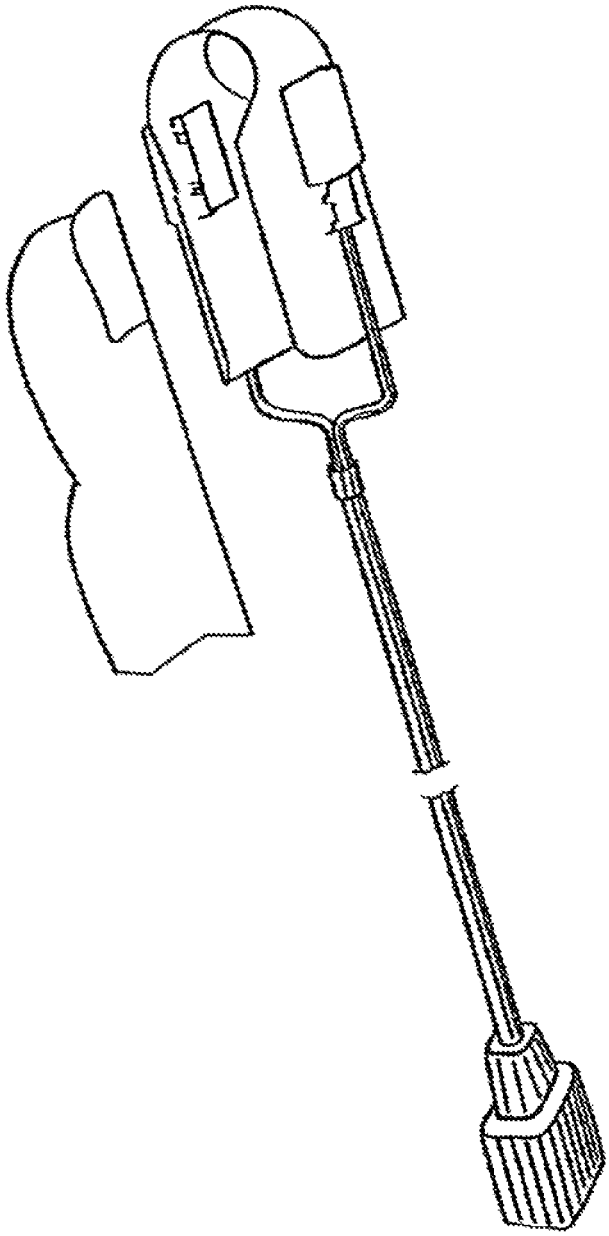

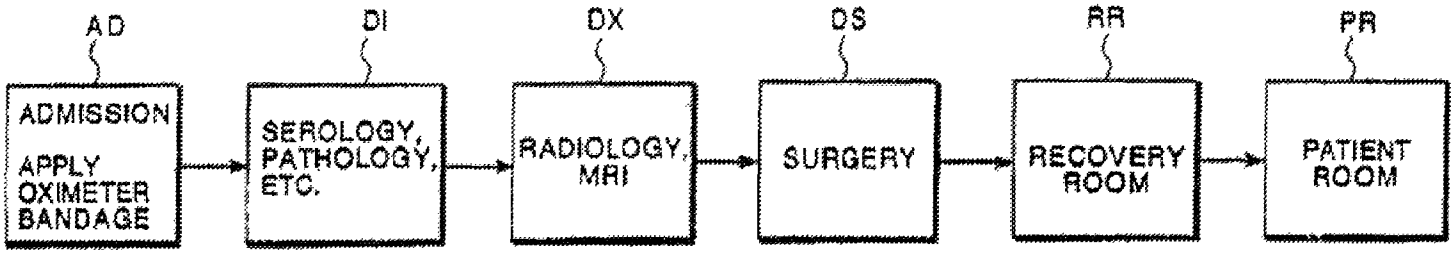
FIG. 9
NEW
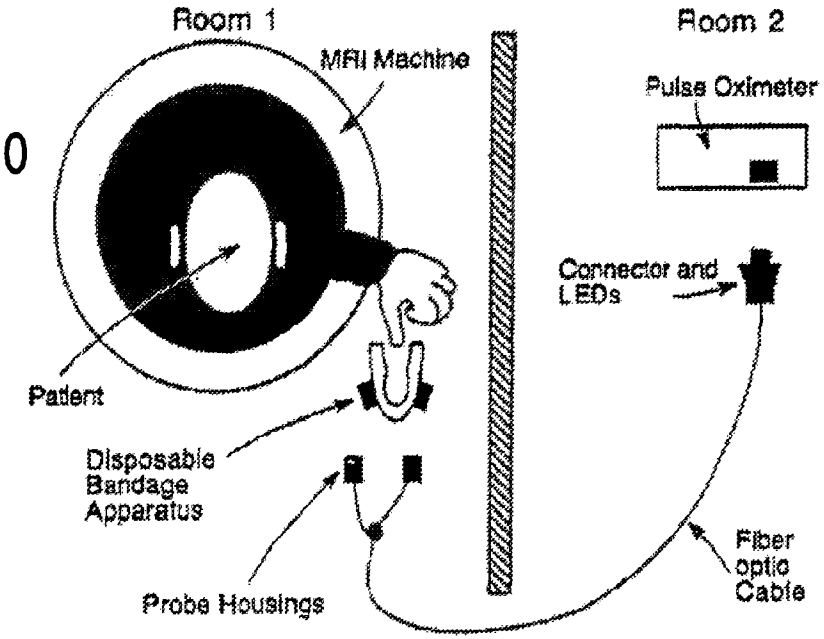
FIG. 10
NEW

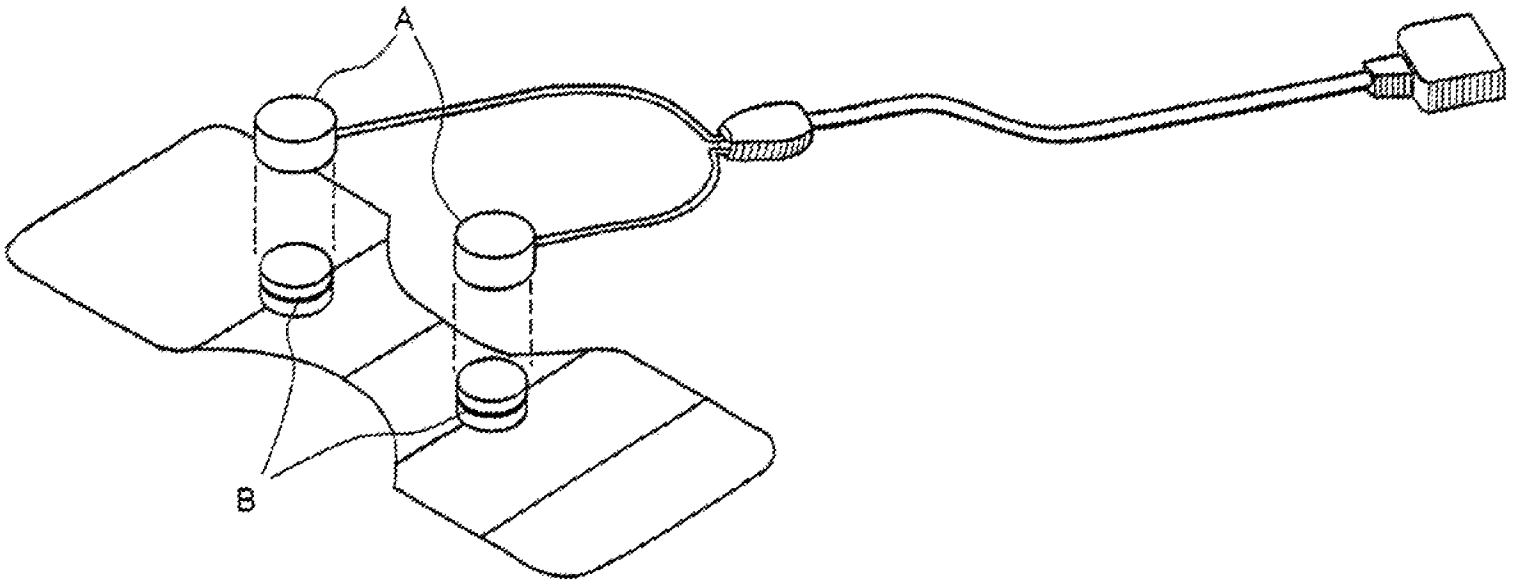
FIG. 11
NEW

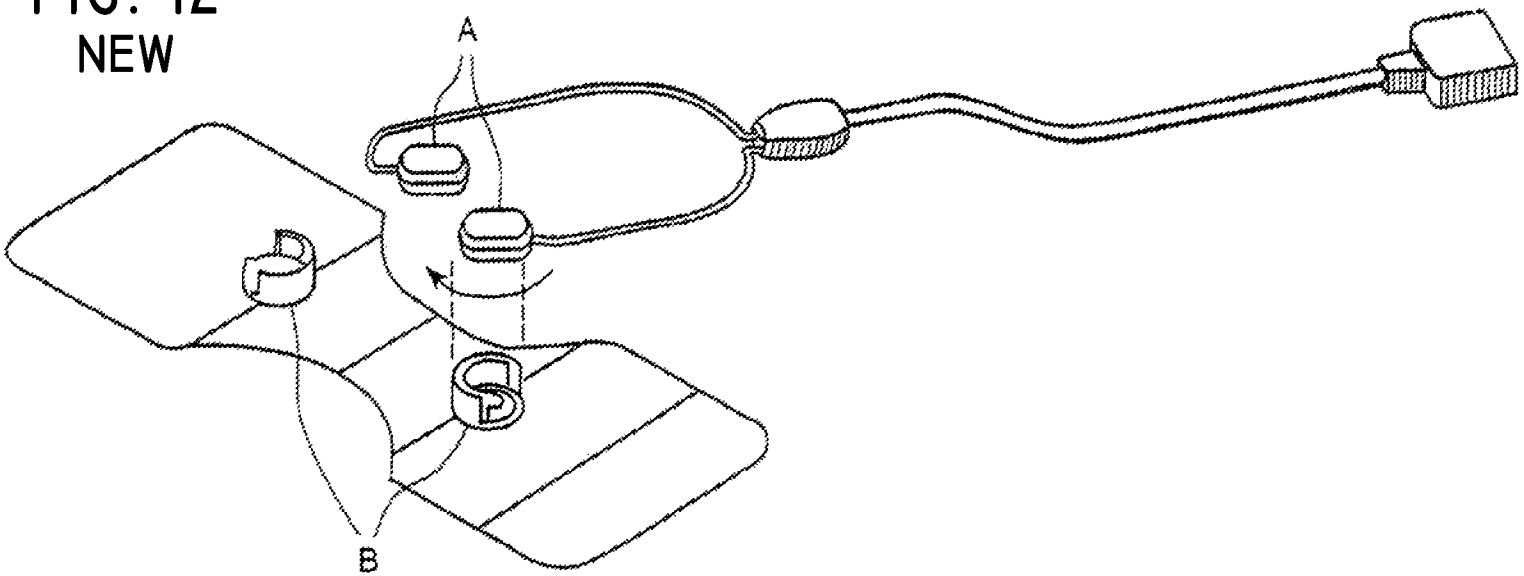
FIG. 12
NEW

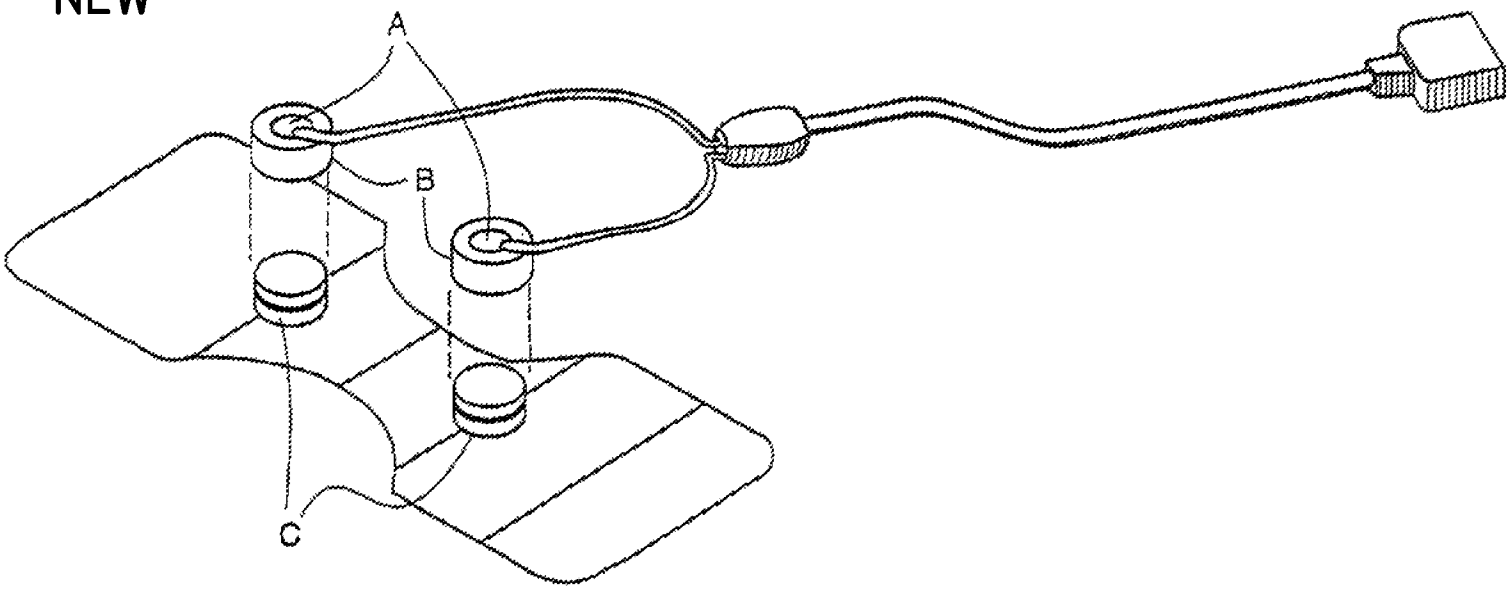
FIG. 13
NEW

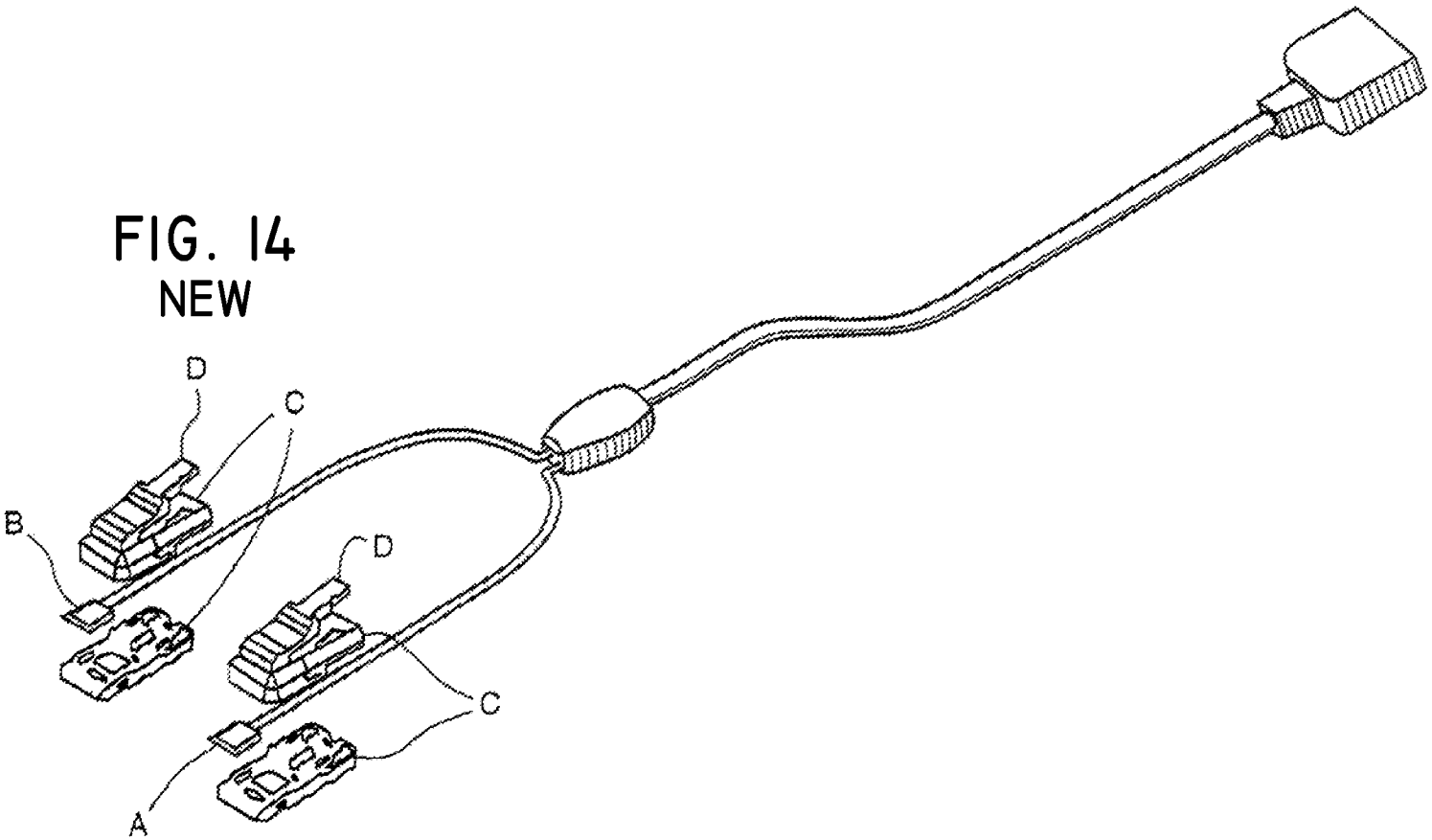
FIG. 14
NEW

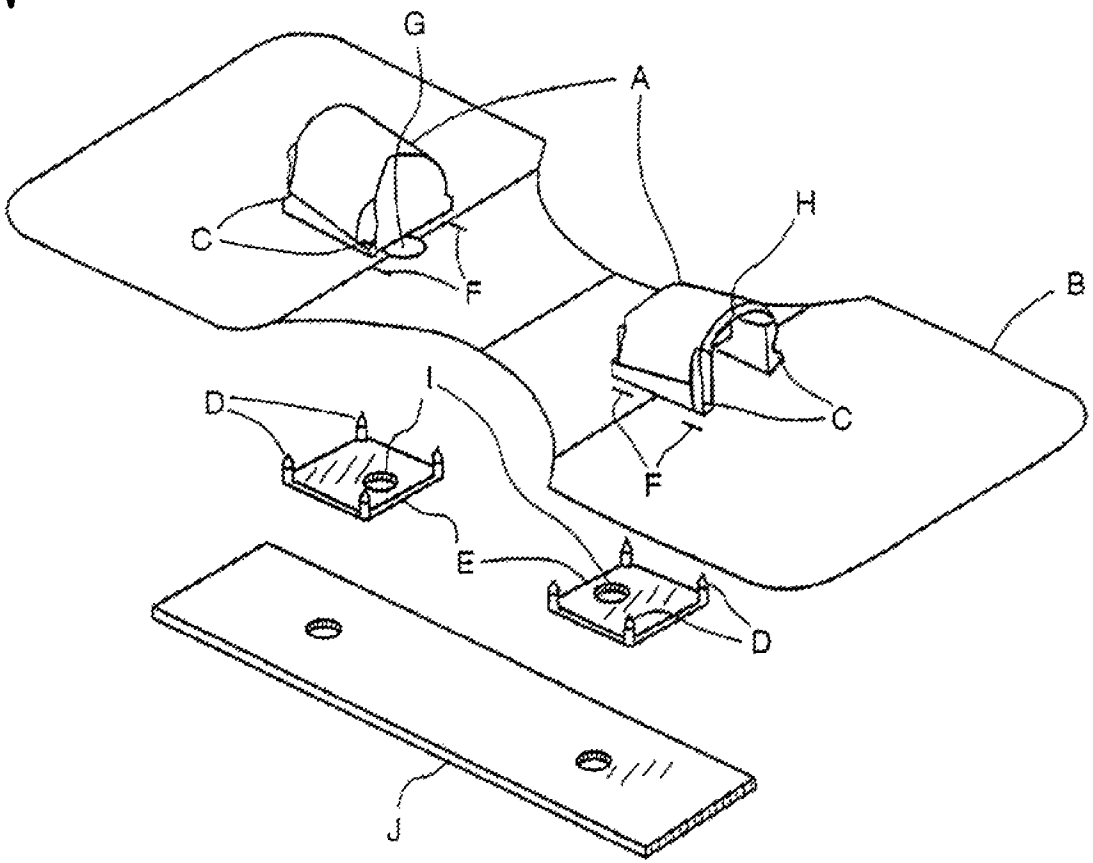
FIG. 15
NEW

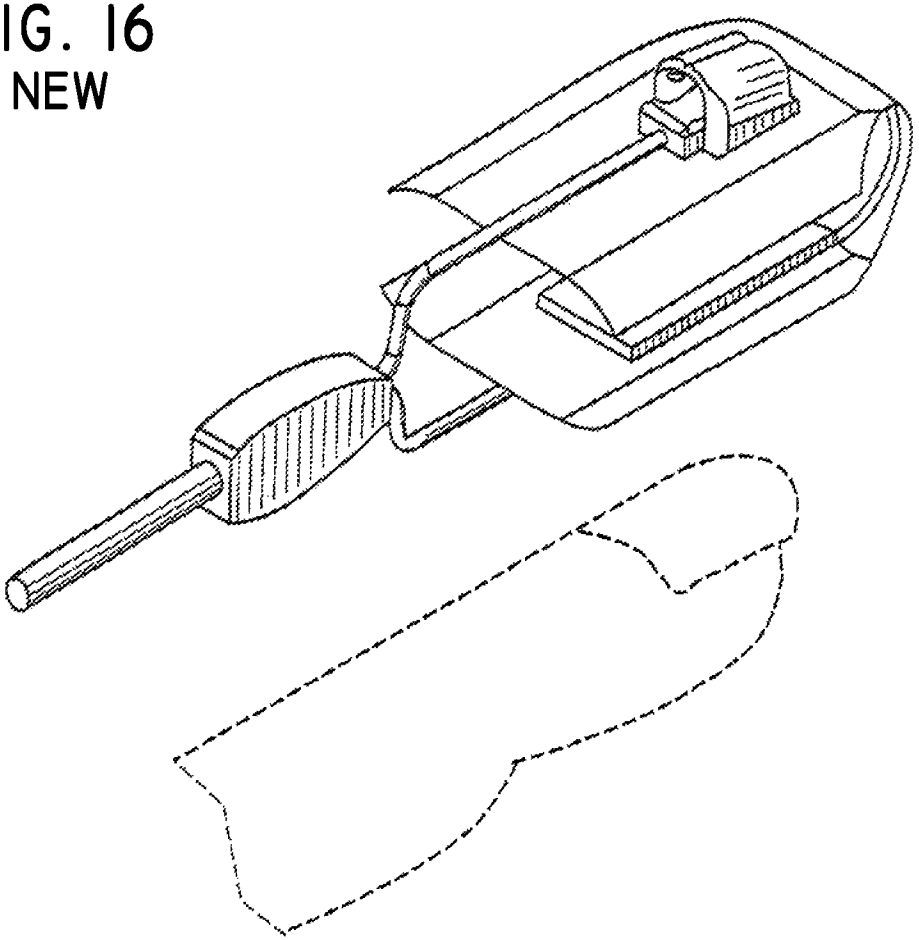
FIG. 16
NEW

FIG. 17
NEW
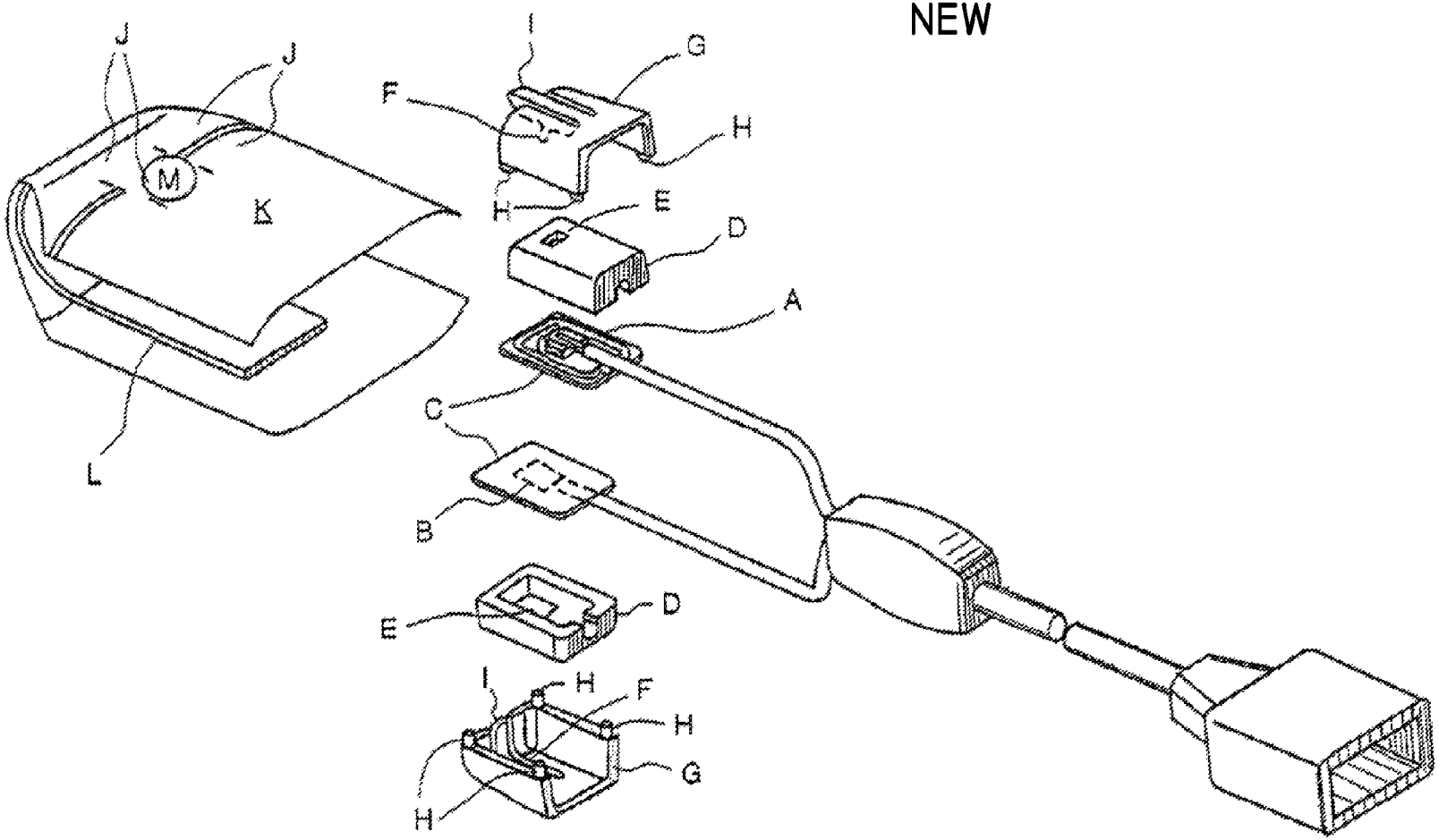

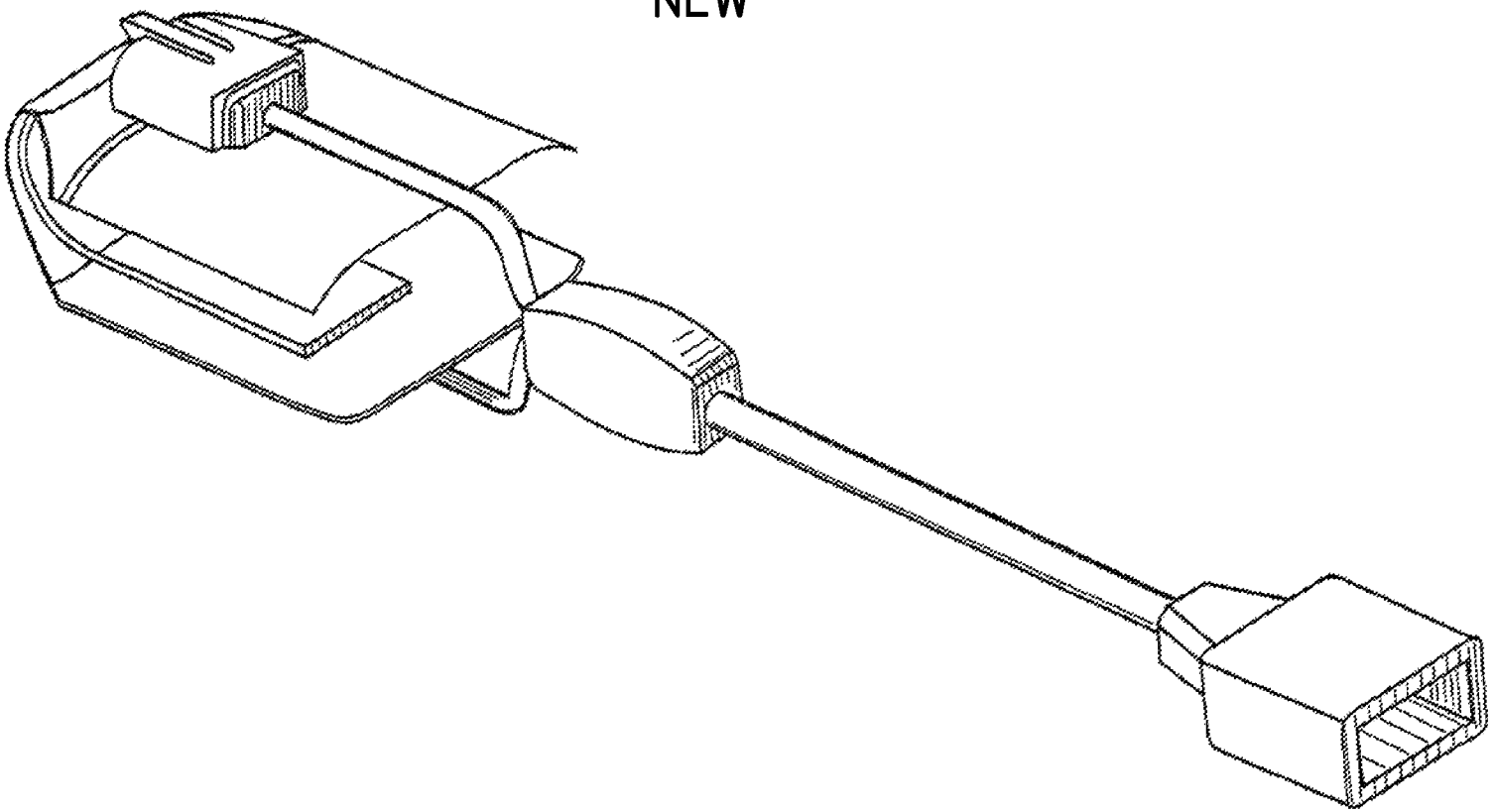
FIG. 18
NEW

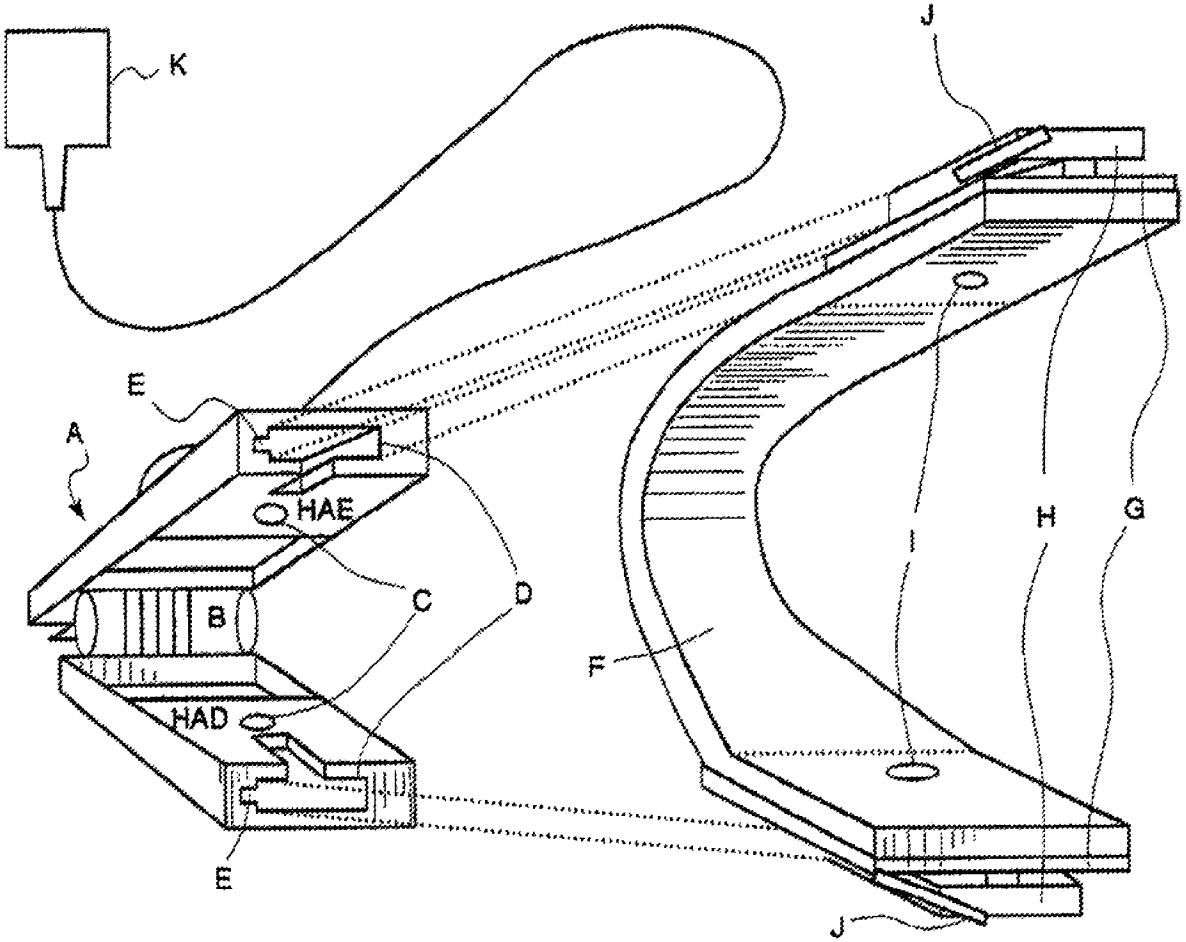
FIG. 19
NEW

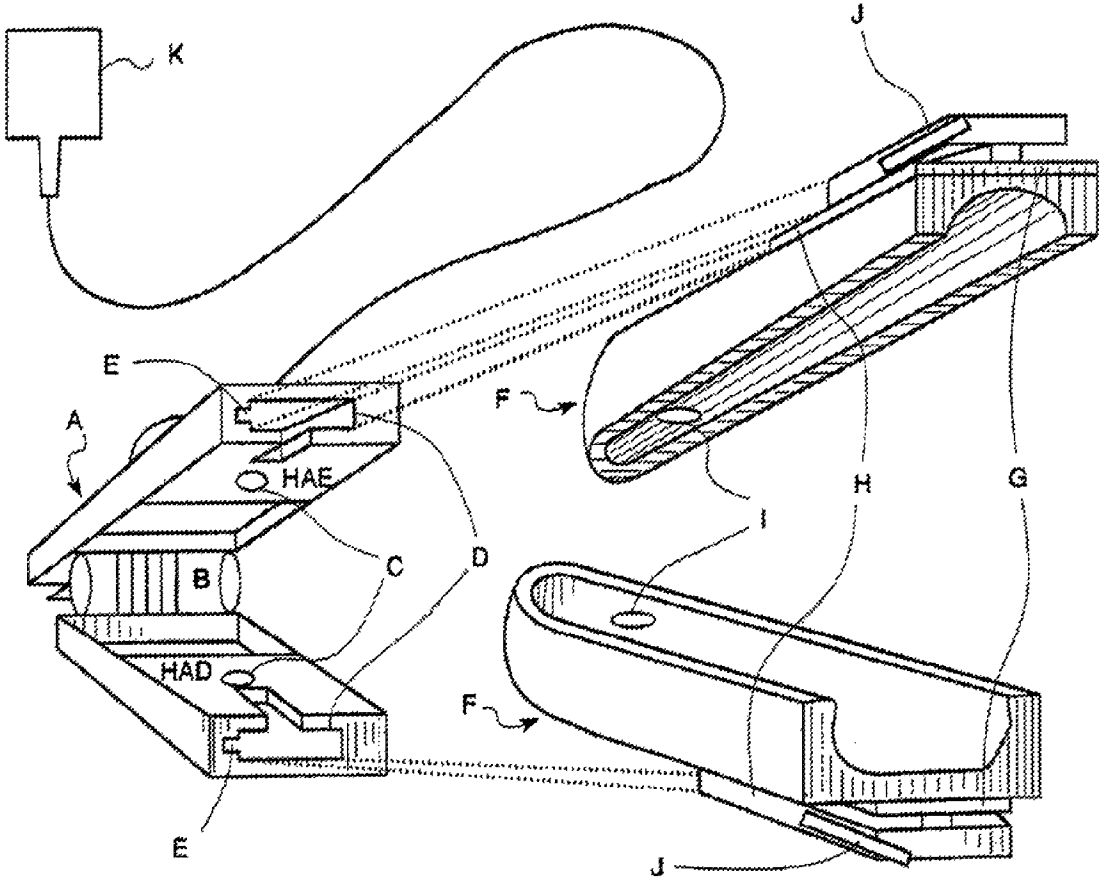
FIG. 20
NEW

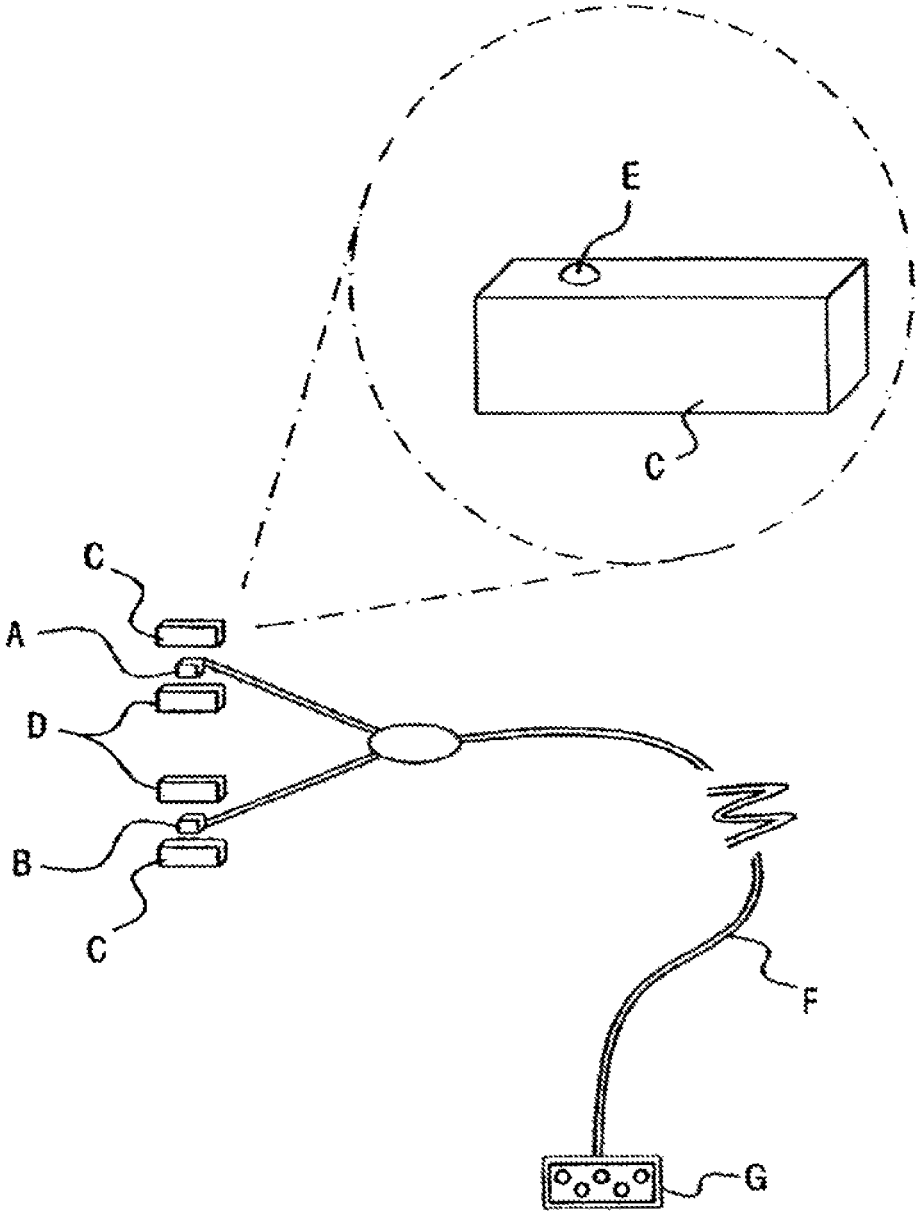
FIG. 21
NEW

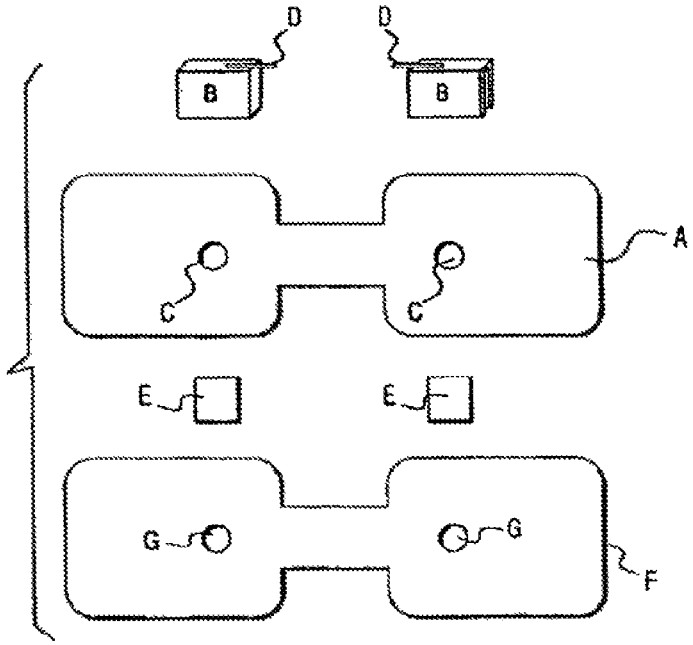
FIG. 22
NEW
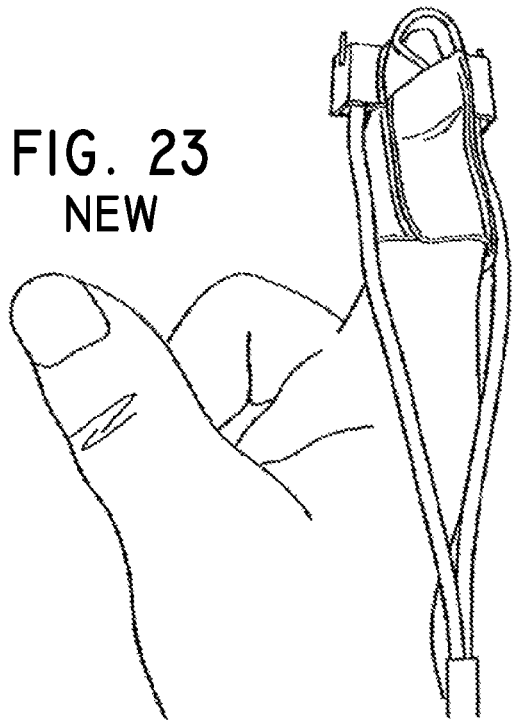
FIG. 23
NEW

FIG. 24
NEW
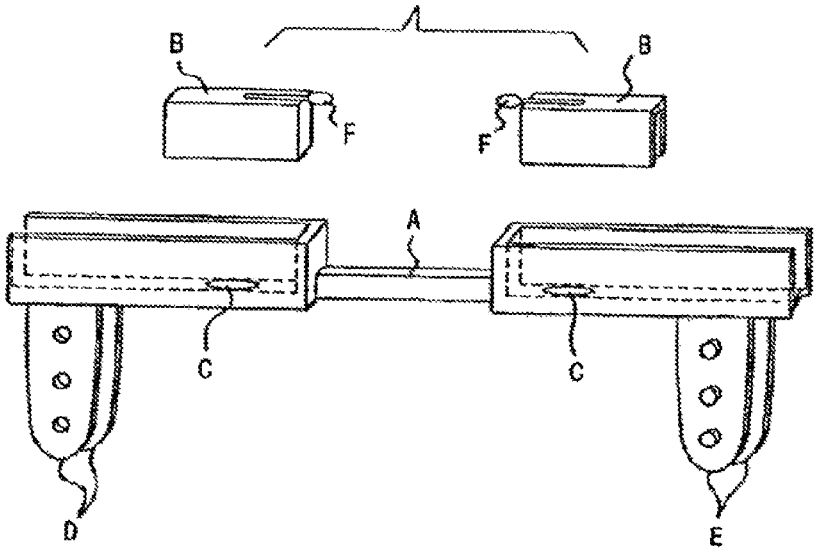
FIG. 25
NEW
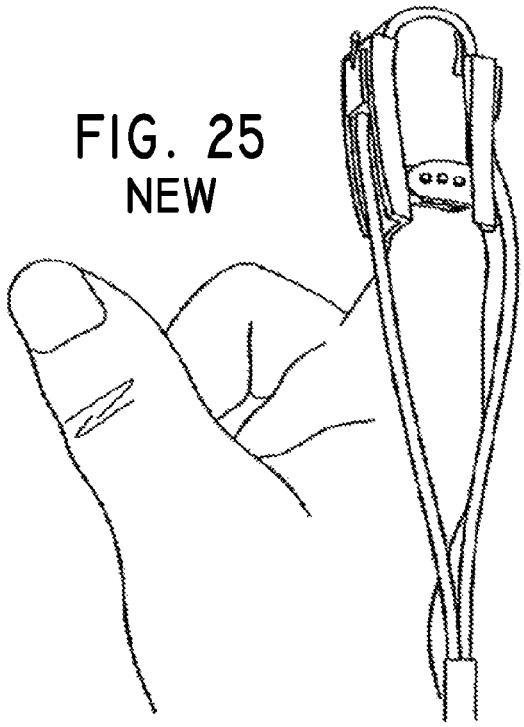

UNIVERSAL MODULAR PULSE OXIMETER PROBE FOR USE WITH REUSABLE AND DISPOSABLE PATIENT ATTACHMENT DEVICES

Matter enclosed in heavy brackets [ ] appears in the original patent but forms no part of this reissue specification; matter printed in italics indicates the additions made by reissue.

REFERENCE TO RELATED APPLICATIONS

*Notice: More than one reissue application has been filed for the reissue of U.S. Pat. No. 6,721,585. The reissue applications are application Ser. No. 11/404,123, filed Apr. 13, 2006, application Ser. No. 12/573,851, filed Oct. 5, 2009, which is a continuation reissue application of the application Ser. No. 11/404,123 and claims the benefit thereof, and the present application, which is a division reissue application of the application Ser. No. 12/573,851 and claims the benefit of both of the prior reissue applications, all three of which are broadening reissues of U.S. Pat. No. 6,721,585.*

[This application] *U.S. Pat. No. 6,721,585* is a continuation-in-part of application Ser. No. 09/417,898, filed Oct. 14, 1999, entitled REUSABLE [PULSES] *PULSE* OXIMETER PROBE AND DISPOSABLE BANDAGE APPARATUS, now U.S. Pat. No. 6,343,224, which in turn is a continuation-in-part of *application* Ser. No. 09/289,647, filed Apr. 12, 1999, entitled REUSABLE PULSE OXIMETER PROBE AND DISPOSABLE BANDAGE APPARATUS [and], now issued as U.S. Pat. No. 6,144,868[,]; and is a continuation-in-part *of* application [of] Ser. No. 09/679,828, filed Oct. 5, 2000, *entitled REUSABLE PULSE OXIMETER PROBE AND DISPOSABLE BANDAGE APPARATUS,* now U.S. Pat No. 6,519,487; and is a [CiP] *continuation-in-part* of *application* Ser. No. 09/352,144, filed Jul. 13, 1999 [and is CiP of], *entitled REUSABLE PULSE OXIMETER PROBE WITH DISPOSABLE LINER,* now U.S. Pat. No. 6,321,100; *and is a continuation-in-part of application* Ser. No 09/758,038, filed Jan. 11, 2001, *entitled REUSABLE PULSE OXIMETER PROBE AND DISPOSABLE BANDAGE METHOD, now U.S. Pat. No. 6,684,091*; each of which is incorporated herein by reference. This application claims benefit of U.S. [provisonal] *provisional* application No. 60/104,332, filed Oct. 15, 1998.

BACKGROUND OF THE INVENTION

*1. Field of the Invention*

*The present invention relates to a method of making and affixing a reusable probe to a patient by means of disposable bandage apparatus so that there is no contact between the costly, reusable portion of the probe and the patient. The contaminated bandage apparatus, which is relatively inexpensive, can then be discarded after single patient use and the probe can be re-used with a new bandage apparatus.*

*2. Description of the Related Art*

Heretofore the use of pulse oximeter probes has been limited to the use of a costly, reusable probe, which is contaminated by use on a patient, or cheaper, single-use probes, which, in the aggregate, amount to a considerable expenditure for a healthcare institution.

*Others have attempted to convert single-use probes into multi-use probes through a lamination process. In that process, the original adhesive material is removed from the original manufacturer's sensor. The sensor is then laminated in a plastic sheath and the entire sheath is then inserted into a transparent, adhesive-backed sleeve, which is then adhered to a patient. After use, the probe can then be extracted from the sleeve and inserted into a new sleeve for use on another patient.*

*There are certain disadvantages to this method. Firstly, it is difficult to insert the flexible laminated sensor into a long sleeve. Secondly, the thickness of a laminated sensor inside of a sleeve makes it difficult to bend around, and to stick properly to, a human appendage. Thirdly, transmission and reception of infrared light can be affected by extraneous light entering from the sides of the sleeve. And, fourthly, there is some dispute as to the affect on infrared light transmission when passing through the sleeve and the adhesive material coupled thereto.*

*One of the problems with pulse oximetry, and the continuity of monitoring a patient, is the vast array of different monitors used in different hospital departments. Many times a patient will start out in the emergency room (ER) where the hospital utilizes one particular brand of monitor. If a disposable probe is affixed to the patient, and the patient is then admitted to intensive care, the disposable probe that was affixed in the ER will only work if the pulse oximeter used in intensive care is of the same make as the one in the ER. If that same patient is once again taken to radiology, or to have an MRI done, once again these different departments may have different pulse oximeter monitors. What happens many times is that the disposable probes affixed in one department are thrown away and new ones are affixed in other departments. Obviously, this creates additional expense in providing pulse oximetry monitoring.*

*SUMMARY OF THE INVENTION*

The current applicant, in his U.S. Pat. No. 6,144,868, and subsequent continuations-in-part, has described a reusable pulse oximeter probe to be used with a disposable bandage apparatus. With this device, the costly reusable portion of the probe is isolated from the patient by means of an inexpensive bandage apparatus. This allows the caregiver to dispose of the inexpensive bandage apparatus while retaining the more costly, reusable portion of the probe. The reusable probe can then be used in conjunction with another disposable bandage apparatus on another patient.

*One embodiment of the present invention is directed to improving the form and affixation method of a reusable pulse oximeter sensor. It comprises a reusable pulse oximeter probe with at least one light emitting diode and one photocell detector wherein said emitter and detector are enclosed in plastic housings, one housing having an aperture or radiation transparent window aligned with said emitter, and the other housing having an aperture or radiation transparent window aligned with said detector. Also included is a disposable bandage apparatus which is at least one bandage strip having adhesive on at least a portion of at least one face thereof and at least two plastic receptacles mounted thereon, each receptacle having at least one aperture or radiation transparent window located therein. The probe housings can matedly engage said bandage receptacles and transmit and receive light through the apertures or radiation transparent windows of said mated housings and receptacles, and through the appendage of a patient. The housings of the reusable pulse oximeter probe may also be made of a material selected from plastic, rubber, metal, wood, or other composite material. The receptacles of the disposable bandage apparatus may also be made of a material selected from plastic, rubber, metal, wood, or other composite material. Additionally, the*

*apertures of said receptacles are large enough to accept the tubular protrusions of the housings for the purpose of concentric location and alignment of the housings to the receptacles and the proper transmission and reception of light therethrough. Sandwiched between the adhesive strip and the receptacles attached thereto, are translucent silicone windows or windows of another radiation transparent material for isolation of the reusable probe assembly from the patient. The bandage apparatus may be discarded after single patient use and the reusable probe may be used again on another patient in conjunction with another bandage apparatus. Additionally, the receptacles of the bandage apparatus may have a concave surface on one side thereof in order to seat conformably on a human digit, or they may have a flat surface on at least one side thereof in order to attach conformably to a human foot, nose, or ear. The housings and receptacles also contain "mushroom hook" type hook and loop material for the purpose of adhering and detaching said housings to and from said receptacles. Additionally, the housings and receptacles have recessed areas for adhesion of the "mushroom hook" hook and loop material.*

*In another embodiment of the invention, the receptacle of the disposable bandage apparatus may be the mushroom hook material itself which may be attached directly to the adhesive strip for the selective engagement of the housings of the probe assembly.*

*In another embodiment of the invention, the housings of the pulse oximeter probe may be affixed to the receptacles of the disposable bandage apparatus by means of a "ring and groove" type snap-on connector.*

*In yet another embodiment of the invention, the housings of the reusable pulse oximeter probe may be affixed to the receptacles of the disposable bandage apparatus by means of a "twist and lock" type connector.*

*In a further embodiment of the invention, the housings of the pulse oximeter probe may be affixed to the receptacles of the disposable bandage apparatus by means of a "threaded flange" type of connector.*

*In a preferred embodiment of the invention, the light emitting diode and photocell detector of the probe assembly may be mounted in modular housings with locking levers which can engage an indentation or slot in the receptacles of the disposable bandage apparatus and securely lock the housings into proper position within the receptacles, thus allowing the transmission and reception of infrared light through the mated housings and receptacles and through the appendage of a patient.*

*In another variation of this preferred embodiment of the invention, the levers and indentations are reversed, and the light emitting diode and photocell detector of the probe assembly may be mounted in modular housings having indentations therein, and the receptacles of the disposable bandage apparatus may have the locking lever located on them. In such an embodiment, the locking levers of the bandage receptacles lockingly engage the slots or indentations in the probe housings, thus locking them into place within the receptacles and allowing the transmission and reception of infrared light through the mated probe housings and bandage receptacles, and through the appendage of a patient.*

*In these modular housing and receptacle embodiments, the radiation transparent windows may be of hard plastic and may be mounted against the skin of a patient, thus being used to secure the receptacles on the opposite side of the bandage strip. This is accomplished by the incorporation of locking levers on the radiation transparent windows which are pushed through holes or slots in the bandage and engage holes in the receptacles mounted on the opposite side of the bandage, thus sandwiching the bandage in between. A foam strip with holes in it may also be adhered to said radiation transparent windows in order for them to rest comfortably on a patient's appendage.*

*In another variation of the above, the bandage receptacles may be secured to the bandage through the use of small plastic protrusions or "heat stakes" mounted on the receptacles themselves. These protrusions can be pushed through slots in the bandage and can be melted on the other side of the bandage strip by means of an ultrasonic welding machine, thus locking the receptacles into position on the bandage strip. In this embodiment a radiation transparent window may then be adhered to the underside of the bandage strip and the heat stakes and radiation transparent windows may then be overlaid with a foam pad with holes in it, the purpose of which is to allow for the transmission and reception of infrared light through the holes while aiding in patient comfort.*

*In some embodiments, one object is to provide a method of facilitating the intra-departmental or inter-institutional transport of a patient or patients requiring the pulse oximeter monitoring, and wherein said pulse oximeters used for monitoring said patient may be of different manufacturers. The method comprises affixing to said patient a bandage apparatus having a modular emitter and detector receptacles incorporated thereon, providing each said different manufacturers' pulse oximeter probe with modular housings adapted to matedly engage and/or disengage with receptacles of the disposable bandage apparatus, thus enabling said patient to be monitored by pulse oximeters of different manufacturers without changing the affixed bandage apparatus.*

*With some embodiments of the present invention, intra-departmental or inter-institutional transport is greatly facilitated by having a bandage device which will accept probes of various manufacturers, as long as those probes contain housings that will matedly engage the receptacles of the disposable bandage apparatus.*

*Another embodiment of the present invention relates to a method of making and affixing a reusable finger probe to a patient by means of a finger clip apparatus with a disposable liner insert so that there is no contact between the costly, reusable portion of the probe and the patient. The contaminated liner, which is relatively inexpensive, can then be discarded after single patient use and the probe and finger clip can be re-used with a new liner. Additionally, such disposable inserts may be provided of different sizes and would greatly enhance the fit and function of the finger clip on the patient. This is important for several reasons. Firstly, a fitted finger clip would be much more comfortable to wear than conventional finger clips. Secondly, a fitted finger clip would allow the transmission and reception of infrared light from the LEDs of the probe without interference from extraneous light sources around the front and edges of the finger, and thirdly, a fitted finger clip would evenly distribute the pressure from the spring of the finger clip and would be much less likely to restrict blood flow to the digit and thereby cause erroneous oxygen saturation readings.*

*Another embodiment of the present invention comprises a method for improving the reusability, fit, and cleanliness of a reusable pulse oximeter finger sensor. It comprises a reusable pulse oximeter probe with at least one light emitting diode and one photocell detector wherein said emitter and detector are mounted in respective finger clip housing arms having apertures therein, one housing arm having an aperture aligned with said emitter, and the other housing arm having an aperture aligned with said detector. Incorporated into each opposing side of the finger clip is a T-shaped channel or slot with a locking protrusion or detent at the entrance of each*

*of the channels. Also included is a disposable foam liner which is an initially, substantially planar, foam strip, having plastic backing on at least a part thereof and two T-shaped protrusions mounted in the lateral plane of said plastic backing. At opposing ends of the foam strip, and incorporated into the T-shaped protrusions, are notched levers for locking the foam strip into position in the T-shaped channel of the finger clip. In the center of the foam strip, the plastic backing is of a thickness that will allow it to bend into a "U" shape for insertion into the finger clip. Alternatively, the plastic backing may be entirely absent and the inherent flexibility of the foam itself will allow it to bend into the desired shape. Additionally, the foam strip contains two apertures located centrally therein containing silicone windows, or windows of another radiation transparent material, that will allow for the transmission and reception of infrared light. Additionally, the foam may also contain an adhesive for helping to adhere the finger clip to the patient.*

*In another preferred embodiment of the invention, the finger clip may be of scaled down design and would allow for the insertion of different sizes of molded foam that would conform in size to the digit on which the finger clip is to be used. In such an application, the foam itself would be intended to substantially envelop the finger and the finger clip would be a mechanism for pinching or biasing the two foam halves together.*

Despite the cost and safety advantages of the reusable probe and disposable bandage apparatus over disposable probes, an increasing number of institutions are beginning to utilize reusable finger clip probes because of the cost savings associated with a completely reusable product. Despite the discomfort of these devices and the risk of spreading infection from patient to patient, the trend toward reusable probes continues to strengthen.

However, in all institutions there is always the need for some disposable probes. Patients who have compromised immune systems, surgical patients, where sterility is important, and neonatal and pediatric patients, where the size of the appendage to be monitored is too small for finger clips, require the use of disposable probes or a disposable bandage apparatus.

Clearly, it would be advantageous to offer a universal, modular, reusable probe that could be used in conjunction with either a reusable finger attachment device or a disposable bandage apparatus, each having receptacles into which the reusable probe could be lockingly engaged and disengaged. In addition, probes from all the different oximeter manufacturers could be standardized so that they could be used in conjunction with these same patient attachment devices.

[THE PRESENT INVENTION]

[The] *One embodiment of the* present invention is directed to a system and a method of standardization of a pulse oximeter probe wherein the probe comprises at least one light emitting diode and at least one photocell detector wherein said emitter and detector are incorporated into modular plastic housings, at least one housing having an aperture or radiation transparent window aligned with said emitter, and at least said second housing having an aperture or radiation transparent window aligned with said detector; wherein said housings can lockingly engage and disengage receptacles mounted on at least either:

(a) a reusable finger attachment device, or (b) a disposable bandage apparatus, and transmit and receive light through the appendage of a patient when either of the above devices are attached to a patient and when the housings of said probe are matedly engaged with the receptacles of the attached device.

The receptacles of the disposable bandage apparatus or the reusable finger attachment device may have locking levers for lockingly engaging and disengaging the modular probe housings.

The probe housings may have indentations or detentes for lockingly engaging and disengaging the levers of the receptacles of the disposable bandage apparatus or reusable finger attachment device.

The disposable bandage apparatus may have radiation transparent windows for the isolation of the probe housings from the patient.

The probe housings may be standardized in size so that probes to fit at least one of a multiplicity of manufacturers' oximeters will incorporate housings that can be matedly engaged with either a reusable finger attachment device or a disposable bandage apparatus.

[What] *According to one embodiment, what* is disclosed is [the] *a* method of supplying pulse oximeter probes compatible with at least one of a multiplicity of manufacturers' oximeters, said probe or probes incorporating standardized probe housings, which can be matedly engaged with at least either a reusable finger attachment device or a disposable bandage apparatus.

*BRIEF* DESCRIPTION OF THE DRAWINGS

The above and other advantages of the invention will become more clear when considered with the following specifications and accompanying drawings wherein:

*FIG. 1 is an exploded view of the reusable pulse oximeter probe and disposable bandage apparatus incorporating one embodiment of the invention;*

*FIG. 2 is a view of the reusable pulse oximeter probe and disposable bandage apparatus shown individually as components of the one embodiment of the invention;*

*FIG. 3 illustrates one embodiment of the invention in use on a human finger or digit;*

*FIG. 4 illustrates an exploded view of another embodiment of the invention in which the "mushroom hook" material itself is used as the receptacle of the disposable bandage apparatus;*

*FIG. 5 illustrates an assembled view of a preferred embodiment of the reusable pulse oximeter sensor in which the light-emitting diode and photocell detector of the reusable probe are mounted in modular housings with locking levers;*

*FIG. 6 illustrates an exploded view of a preferred embodiment of the reusable pulse oximeter sensor;*

*FIG. 7 illustrates an exploded view of a preferred embodiment of a bandage apparatus in which the receptacle tops incorporate a slot for engaging the locking levers of modular probe housings, and wherein radiation transparent windows are mounted on the opposite side of the bandage strip, thus sandwiching and securing the bandage in between the two receptacle halves by means of locking levers;*

*FIG. 8 illustrates a preferred embodiment of the invention as it would appear ready for use on a human digit;*

*FIG. 9 is a patient flow diagram showing the intra-departmental or inter-institutional transport of a patient;*

*FIG. 10 is a schematic illustration of how probe housings can utilize fiberoptic cable connecting a light emitter and detector to a disposable bandage according to one embodiment of the invention;*

*FIG. 11 illustrates an assembled view of another embodiment of the invention in which the housings of the pulse*

*oximeter probe are affixed to the receptacles of the disposable bandage apparatus by means of ring and groove type, snap-on connectors;*

*FIG. 12 illustrates an assembled view of another embodiment of the invention in which the housings of the pulse oximeter probe are affixed to the receptacles of the disposable bandage apparatus by means of "twist and lock" type connectors;*

*FIG. 13 illustrates an assembled view of another embodiment of the invention in which the housings of the of the pulse oximeter probe are affixed to the receptacles of the disposable bandage apparatus by means of a "threaded flange" type of connector;*

*FIG. 14 illustrates an exploded view of a preferred embodiment of the reusable pulse oximeter probe in which the light emitting diode and photocell detector of the probe are encased in housings having a radiation transparent window therein and locking levers for affixing the reusable pulse oximeter probe to the disposable bandage apparatus;*

*FIG. 15 illustrates an exploded view of a preferred embodiment of the disposable bandage apparatus in which the receptacle tops incorporate a slot for engaging the locking levers of the modular probe housings, and wherein the radiation transparent windows are mounted on the opposite side of the bandage strip, thus sandwiching and securing the bandage in between the two receptacle halves by means of locking tabs or heat stakes that can be ultrasonically welded;*

*FIG. 16 illustrates a preferred embodiment of the invention as it would appear ready for use on a human digit;*

*FIG. 17 illustrates an exploded view of another preferred embodiment of the invention in which the probe housings have a slot or indentation incorporated therein and the bandage receptacles have a locking lever for securing the housings to the receptacles;*

*FIG. 18 illustrates an assembled view of one embodiment of the invention in which the probe housings have a slot or indentation incorporated therein and the bandage receptacles have a locking lever for securing the housings to the receptacles;*

*FIG. 19 is an exploded view of a standard pulse oximeter probe and finger clip with disposable liner;*

*FIG. 20 is an exploded view of one preferred embodiment of the invention incorporating two disposable liners having finger conformance;*

FIG. [1] *21* is a exploded view of a pulse oximeter probe incorporating modular plastic housings[.]*;*

FIG. [2] *22* is an exploded view of a disposable bandage apparatus incorporating modular plastic receptacles[.]*;*

FIG. [3] *23* is a view of the disposable bandage apparatus with the probe engaged and in use on the appendage of a patient[.]*;*

FIG. [4] *24* is an exploded view of a reusable finger attachment device incorporating modular plastic receptacles[.]*;* and FIG. [5] *25* illustrates the reusable finger attachment device, with the probe engaged, and in use on a human appendage.

*DETAILED DESCRIPTION OF THE PREFERRED EMBODIMENTS*

*Reusable Pulse Oximeter Probe and Disposable Bandage Apparatuses and Methods*

*Description of a Reusable Pulse Oximeter Sensor*

*The reusable pulse oximeter sensor constitutes a "Y" style pulse oximeter probe shown in FIG. 1, Item F. The probe incorporates two plastic housings shown as FIG. 1, Items G. The housings contain apertures or radiation transparent windows L therein. One housing contains the light-emitting diode of the probe, FIG. 1, Item H, and other contains the photocell detector, FIG. 1, Item I. The emitter and detectors are aligned with the apertures or windows L of the housings in order to transmit and receive light through a human appendage.*

*Seated within a recessed area of each housing, and attached permanently thereto, is a "mushroom hook" adhesive-backed pad, FIG. 1, Item K. The purpose of these pads is to selectively engage the "mushroom hook" pads, FIG. 1, Items J, attached permanently to the plastic discs, FIG. 1, Items D, and to attach the reusable probe assembly to the Disposable Bandage Apparatus. The reusable pulse oximeter sensor is shown assembled as FIG. 2, Item A.*

*In one preferred embodiment of the reusable pulse oximeter sensor, the light-emitting diode (FIG. 5, Item A) and photocell detector (FIG. 5, Item B) of the probe assembly are housed in modular receptacles (FIG. 5, Items C) having locking levers (FIG. 5, Items D) for engaging the receptacles of the disposable bandage apparatus, and locking them into place. In this embodiment, the light-emitting diode (FIG. 6, Item A) and the photocell detector (FIG. 6, Item B) are sandwiched between interlocking receptacle halves, the bottom halves of which (FIG. 6, Items C) are made of a radiation transparent material.*

*In another embodiment of the invention the light emitting diode and photocell detector of the reusable pulse oximeter sensor are enclosed in housings (FIG. 11, Items A) having a groove on the inner diameter of the housings that is designed to matedly engage rings (FIG. 11, Items B) located on the outer diameter of the disposable bandage apparatus, thus securing and locking the sensor housings to the bandage receptacles.*

*In another embodiment of the invention the light emitting diode and photocell detector of the reusable pulse oximeter sensor are enclosed in housings (FIG. 12, Items A) which are designed to enter the bandage receptacles (FIG. 12, Items B) and to twist 90 degrees thus locking the sensor housings to the bandage receptacles.*

*In yet another embodiment of the invention, the light emitting diode and photocell detector of the reusable pulse oximeter sensor are enclosed in housings (FIG. 13, Items A) having a threaded flange (FIG. 13, Items B) that threadedly engages the bandage receptacles, (FIG. 13, Items C) thus securing and locking the sensor housings to the bandage receptacles.*

*In the one preferred embodiment of the Reusable Pulse Oximeter Sensor, the light emitting diode (FIG. 14, Item A) and photocell detector (FIG. 14, Item B) of the probe assembly are housed in modular receptacles (FIG. 14, Items C) having locking levers, (FIG. 14, Items D) for engaging the receptacles (FIG. 15, Items A) of the disposable bandage apparatus, and locking them into place.*

*In the another preferred embodiment of the Reusable Pulse Oximeter Sensor, the light emitting diode (FIG. 17, Item A) and the photocell detector (FIG. 17, Item B) are encased in modular housings having a radiation transparent bottom (FIG. 17, Items C) and having opaque housing tops (FIG. 17, Items D). These housing tops and bottoms are ultrasonically welded together thus encapsulating the light emitting diode and photocell detector of the probe assembly. The housing tops incorporate indentations or slots (FIG. 17, Items E) designed to matedly engage a protrusion on the locking levers of the bandage receptacles thus snapping into place and securing the probe housings within the bandage receptacles.*

*According to one embodiment of the present invention, intra-departmental or inter-institutional transport is greatly facilitated by having a bandage device which will accept probes of various manufacturers, as long as those probes*

*contain housings that will matedly engage the receptacles of the disposable bandage apparatus.*

*Description of a Disposable Bandage Apparatus*

*The components of the apparatus include an adhesive-backed strip, shown as FIG. 1, Item A, the strip A incorporating two oval protrusions B centered thereon and shown as FIG. 1. The strip also incorporates two apertures, centrally located within the oval protrusions, each aperture C having a diameter sufficient in size to accommodate the transmission and reception of light from a light-emitting diode and photocell detector of a pulse oximeter probe.*

*On top of the apertures C are seated two plastic discs, FIG. 1, Item D, each having a concave base designed to conform to the radius of a human digit, and an aperture of slightly larger diameter than the apertures in the adhesive backed planar strip. The plastic discs are affixed to the adhesive planar strip by means of a permanent adhesive.*

*Seated in a recessed area on top of each plastic disc is a "mushroom hook", adhesive backed pad shown as FIG. 1, Item J. The purpose of the "mushroom hook" pads is to selectively engage the "mushroom hook" pads attached to the probe, FIG. 1, Items K, and to attach the probe to the disposable bandage apparatus. Sandwiched between the two plastic discs and the planar adhesive strip are two translucent silicone windows, FIG. 1, Item E. The windows are designed to permit the passage of infrared light and yet prevent contact between probe and patient, and consequently, contamination of the reusable probe itself.*

*The above items constitute the disposable bandage apparatus according to one embodiment of the invention, the apparatus being shown assembled as FIG. 2, Item B.*

*In another embodiment of the invention, the disposable bandage apparatus may be configured as in FIG. 4 of the drawings. FIG. 4 is an exploded view of the apparatus in which the "mushroom hook" pads of the bandage apparatus, FIG. 4, Items J, are bonded directly to the adhesive planar strip, FIG. 4, Item A, for the selective engagement of the "mushroom hook" pads of the probe, FIG. 4, Items K, the pads being attached permanently to the housings of the probe, FIG. 4, Items G.*

*In one preferred embodiment of the disposable bandage apparatus, the bandage strip (FIG. 7, Item A) is sandwiched between interlocking receptacle halves. The top halves of the receptacles (FIG. 7, Items B) contain locking levers (FIG. 7, Items C) that are pushed through slots cut in the bandage strip (FIG. 7, Items D) and lockingly engage indentations (FIG. 7, Items E) in the bottom halves of the receptacles (FIG. 7, Items F), thus sandwiching and locking the bandage in between. The bandage strip contains two apertures (FIG. 7, Items G) for the transmission and reception of light from the light-emitting diode and photocell detector of the pulse oximeter sensor which are encased in modular housings having locking levers (FIG. 5, Items D) wherein the levers engage slots in the receptacles (FIG. 7, Items H) thereby locking the housings into place within the receptacles. In addition, the bottom halves of the receptacles (FIG. 7, Items F) are of a radiation transparent material, thus allowing the light-emitting diode and photocell detector contained in the probe housings, when engaged in the bandage receptacles, to transmit and receive light through the apertures of the bandage strip and through the radiation transparent material of the bottom halves of the receptacles, and through the appendage of a patient. The complete reusable pulse oximeter probe and bandage assembly is shown assembled and ready for use on a human digit in FIG. 8.*

*In other embodiments of the disposable bandage apparatus, the bandage may have mounted thereon receptacles having means of matedly engaging the housings of the reusable pulse oximeter sensor by way of "ring and groove"snap-on type connectors (FIG. 11, Items B); "Twist and Lock" type connectors (FIG. 12, Items B); or "threaded flange" type connectors (FIG. 13, Items C).*

*In one preferred embodiment of the Disposable Bandage Apparatus, the bandage strip (FIG. 15, Item B) is sandwiched between interlocking receptacle halves. The top halves of the receptacles (FIG. 15, Items A) each contain 4 holes (FIG. 15, Items C) that are designed to matingly engage locking tabs (FIG. 15, Items D) on the bottom half of the receptacles (FIG. 15, Items E) that are pushed through slots cut in the bandage strip (FIG. 15, Items F) thus securing and locking the bandage in between.*

*The bandage strip contains two apertures or radiation transparent windows (FIG. 15, Items G) allowing for the transmission and reception of light from the light emitting diode and photocell detector of the pulse oximeter sensor which are encased in modular housings having locking levers (FIG. 14, Items D) wherein said levers engage slots in the receptacles (FIG. 15, Items H) thereby locking the housings into place within the receptacles. In addition, the bottom halves of the receptacles (FIG. 15, Items E) can be of a radiation transparent material, or may contain apertures (FIG. 15, Items I) thus allowing the light emitting diode and photocell detector contained in the probe housings, when engaged in the bandage receptacles, to transmit and receive light through the apertures of the bandage strip and through the radiation transparent material, or apertures, of the bottom halves of the receptacles, and through the appendage of a patient. The disposable bandage apparatus may also incorporate a foam strip (FIG. 15, Item J) in order to cushion a patient's appendage from any discomfort caused by the bottom half of the bandage receptacles. The complete Reusable Pulse Oximeter Sensor, engaged in the disposable Bandage Apparatus, and ready for use on a human appendage, is shown in FIG. 16.*

*In another preferred embodiment of the disposable bandage apparatus, the bandage receptacles (FIG. 17, Items G) are secured to the bandage (FIG. 17, Item K) by means of four protrusions or "heat stakes" (FIG. 17, Items H) which are pushed through slots (FIG. 17, Items J) on the bandage (FIG. 17, Item K) and are ultrasonically welded on the other side, thus securing the receptacles to the bandage. A radiation transparent window (FIG. 17, Item M) is then adhered to the underside of the bandage and the radiation transparent windows and melted heat stakes are then overlaid by a foam pad (FIG. 17, Item L) to aid in patient comfort. This foam pad also incorporates two holes which are in alignment with the two holes on the bandage itself, and when the foam pad is overlaid on the underside of the bandage, the radiation transparent windows are sandwiched in between.*

*The probe housings are designed to matedly engage the bandage receptacles (FIG. 17, Items G) and are held in place within the receptacles by means of protrusions (FIG. 17, Items F) on the locking levers (FIG. 17, Items I) which snap into place when the probe housings are pushed into the bandage receptacles. When the probe housings are locked into place within the bandage receptacles the light emitting diode and photocell detector are in alignment with the holes in the bandage and the foam overlay, and the probe is then able to transmit and receive light through the mated housings and receptacles, through the holes contained in the bandage and foam overlay, and through the appendage of a patient. The complete assembled Reusable Pulse Oximeter Sensor engaged within the Disposable Bandage Apparatus, as it would appear ready for use on a patient, is shown in FIG. 18.*

*Other Fastening Means*

*As can be appreciated, there are many ways of fabricating the above components of the invention. The above description describes attachment of the reusable pulse oximeter sensor to the disposable bandage apparatus by way of a "mushroom hook" type hook and loop material and by the use of telephone type modular connectors and receptacles. In addition to this means, a number of other methods may be used including standard hook and loop material, "ring and groove" type snap-on connectors, "push and twist" type Luerlock connectors, and threaded flange type connectors. While these means are fairly comprehensive, they should in no way be considered exhaustive.*

*Method of Use*

*According to one method for use on an individual patient, the probe is affixed in the following manner:*

*Firstly, the backing is removed from the adhesive strip of the disposable bandage apparatus. One of the apertures of the apparatus is visually positioned on the center of the nail bed of the patient's appendage and one side of the adhesive strip and the oval protrusions are adhered to the patient's digit. The rest of the strip is then looped over the end of the patient's appendage, and the plastic disc is aligned so as to exactly oppose the plastic disc already attached to the other side of the digit. Once the disposable bandage apparatus has been properly adhered to the patient, the plastic housings of the probe assembly can be easily snapped into place on opposing sides of the digit. The entire assembled probe is shown as it would appear in use on a patient in FIG. 3.*

*According to one method for use with the "ring and groove" type snap-on connectors, "twist and lock", and "threaded flange" connectors, the backing is firstly removed from the adhesive strip. The strip is then folded in half where indicated on the bandage and the bandage apparatus is adhered to either side of the human digit. Once the bandage apparatus is in place the probe housings are simply snapped, twisted or screwed into place.*

*According to one method for use with a patient, the modular probe and bandage assembly, which is one preferred embodiment of the invention, would be attached as follows:*

*Firstly, the backing is removed from the adhesive strip. The strip is then folded where indicated on the bandage and the strip is then adhered to opposing sides of the human digit. Once the bandage apparatus is in place, the housings of the probe are pushed into the receptacles and locked in place by means of the locking levers. When the patient is moved between different service areas of a hospital, the probes can be removed and the patient transported to a new service area where that area's oximeter probes are pushed into the receptacles for further oximeter readings.*

*As shown in FIG. 9, one embodiment of the invention is easily adaptable to different manufacturers' oximeters being used in different departments or institutions when the patient is to be transported between the departments or institutions. As shown in FIG. 9, at the admissions area AD, when the patient is admitted to the hospital or facility, an oximeter bandage is initially applied. Then the patient may go through another testing area or department D1 where various serological, pathological tests may be run. Then the patient is shown as being transported to a radiology area such as where X-ray and magnetic resonance images (MRI) scans are made. Other departments may have the patient transported thereto such as a surgery department DS and a recovery room RR and the patient's room PR where, in each instance, a different manufacturer or different oximeter probes may be attached where, according to the invention, the receptacles on the bandages are able to receive and retain housings on the emitter and detector elements of the probe.*

*An example of the flexibility of the system of this invention is illustrated in FIG. 10. In this pictorial embodiment, a magnetic resonance image system or an MRI machine is shown as being positioned in one room with the patient and having applicant's disposable bandage apparatus attached to the finger of a patient. In this case, the patient is in the MRI facility where the patient is just having MRI work done. The probe housings are shown attached at the ends of fiberoptic cable connected to a connector which has the light-emitting diode and the light detector incorporated therein with a connector or plug for plugging into a pulse oximeter PO. The light-emitting and light-receiving ends of the fiberoptic cable are directed or oriented in the modular housings to emit IR light into the finger and receive IR light transmitted through the finger. It will be noted that since in the MRI application no ferrous materials are allowed, the LED's are placed in a room many feet away (up to fifty or more feet away) and (the oximeter device is in optical communication with the applicant's bandage apparatus. Thus, in situations where non-ferrous materials are required, the probe has non-ferrous housings and materials designed to matedly engage with the receptacles of applicant's disposable bandage apparatus. The housings of the probe are in fiberoptic communication with the LED's which would be at the other end of the probe near the pulse oximeter.*

*As shown above, in case of magnetic resonance imaging (MRI) situations where the presence of any metal in the environment can effect the MRI readings, the probe and emitter elements are situated remotely from the MRI machine and fiberoptic cable conveys light to and from the patient's finger. In this case, the oximeter probe housings are the termination ends of the fiberoptic cable and the modular housings are therefore able to be inserted into the bandage receptacles and the oximeter readings taken in this fashion from a remote area.*

*In some embodiments of the invention, when the probe is no longer required on the patient, the housings of the reusable probe are simply unsnapped from the disposable bandage apparatus, the bandage apparatus is thrown away, and the probe can then be reused on a new patient in conjunction with a new bandage apparatus.*

*Advantages of Some Embodiments*

*Current reusable pulse oximeter probes are either "clam shell" type clamping devices which can restrict circuit or "Y" type probes which are taped directly to the patient. Both types also come in direct contact with the patient's skin and bodily fluids and need sterilization after use. Because of the fact that these devices incorporate many surfaces and at times, porous materials, proper sterilization is very difficult. With some embodiments of the present invention there is no contact between the reusable probe and the skin or bodily fluids of the patient.*

*Disposable probes are very costly because of the fact that the cable, connectors and photodiodes are all disposed of after use. Some embodiments of the present invention accomplishe the same goals as a disposable probe from a cleanliness standpoint, but since only the attachment apparatus is discarded after use, the cost is much less to a healthcare institution.*

*One embodiment of the present invention, with the concave shape of the plastic discs of the bandage apparatus, when backed by the adhesive strip, is extremely effective in preventing the entrance of extraneous light from the sides of the patient s digit. Current probes on the market, whether dispos-*

*able or reusable, because of the nature of their shape and affixation means, have problems in dealing with extraneous light reception.*

*One embodiment of the present invention utilizes an easy snap-on, snap-off, or modular connector attachment means for attaching the probe to the disposable bandage apparatus. Probe-shield type devices available in the past not only required the modification of the original manufacturer's probe, but required the difficult procedure of inserting a flexible laminated probe into a sheath for each patient.*

*Probe-shield devices, because of the lamination process involved, raised some concern over the transmission and reception of infrared light through the laminating material. One embodiment of the present invention uses a silicone window for the isolation of the probe from the patient. Infrared light transmission and reception is not affected by passage through translucent silicone.*

*In these days of environmental consciousness, the annual waste generated from tens of millions of disposable probes is enormous. Some embodiments of the present invention, if used in considerable numbers, would greatly reduce the amount of environmental waste generated by disposable pulse oximeter probes.*

*In some embodiments, intra-departmental or inter-institutional transport is greatly facilitated by having a bandage device which will accept probes of various manufacturers, as long as those probes contain housings that will matedly engage the receptacles of the disposable bandage apparatus.*

*Reusable Pulse Oximeter Probe with Disposable Liner*

*Description of a Reusable Pulse Oximeter Probe*

*According to one embodiment, the Reusable Pulse Oximeter Sensor constitutes a finger clip style pulse oximeter probe shown as FIG. 19, Item A. The probe incorporates two plastic housing arms, each housing arm containing apertures therein, said apertures shown as FIG. 19, Items C. One housing (HAE) contains the light emitting diode of the probe, and the other (HAD) contains the photocell detector. The emitter and detectors are aligned with the apertures of said housings in order to transmit and receive light through a human appendage. The housings are held together by a pin incorporating a spring, FIG. 19, item B, which inclines the two housings toward each other and clamps the apparatus on a human digit.*

*Within each housing is a "T" shaped channel, FIG. 19, item D, with a locking notch at the entrance thereof, said notch shown as FIG. 19, items E. The purpose of the channel and notch is to slidably engage the disposable liner of the finger clip and to lock it into its appropriate position within the finger clip. The probe is attached to a pulse oximeter through a connector, FIG. 19, item K. The above description constitutes the Reusable Pulse Oximeter Probe component of the invention.*

*Description of a Disposable Liner or Shield*

*According to one embodiment, the components of the disposable liner or shield include an initially planar foam strip shown as FIG. 19, item F, incorporating two apertures, centrally located within the strip, and shown as FIG. 19, Items I, Each aperture has a diameter sufficient in size to accommodate the transmission and reception of light from a light emitting diode and photocell detector of the reusable pulse oximeter probe. Each aperture has a silicone window, or window of another material, which will allow for the transmission and reception of infrared light therethrough.*

*On either end of the foam strip there is a thin plastic backing, FIG. 19, items G, having a "T" shaped protrusion mounted in the lateral plane thereof and shown as FIG. 19, item H. The purpose of the "T" shaped protrusion is to slidably engage the "T" shaped channel of the reusable sensor, FIG. 19, item D, and to lock into place by means of the locking levers, FIG. 19, items J, a releasable detent.*

*In one preferred embodiment of the invention, there are two disposable foam liners, with finger-shaped indentations therein, said indentations varying in size depending on the size of the patient's digit on which they are intended to be used. In this embodiment, the foam liners, FIG. 20, items F, have a plastic backing, FIG. 20, items G. The plastic backings have "T" shaped protrusions mounted thereon, FIG. 20, items H, which slidably engage the "T" shaped channel of the finger clip, FIG. 20, items D, the locking levers, FIG. 20, items J, engaging the locking notches of the finger clip, FIG. 20, items E, and securing the foam into place.*

*Other Fastening Means*

*As can be appreciated there are many ways of attaching the Disposable Liner or Shield to the Reusable Pulse Oximeter Probe. The above description describes attachment of the Disposable Liner to the Reusable Pulse Oximeter Probe by way of a modular type sliding connector. In addition to this means a number of other methods may be used including, hook and loop material, snap-on connectors, and removable adhesive.*

[DESCRIPTION OF THE MODULAR PULSE OXIMETER PROBE]

*Universal Modular Pulse Oximeter Probe for Use with Reusable and Disposable Patient Attachment Devices*

*Description of a Modular Pulse Oximeter Probe*

[The] *According to one embodiment, the* Modular Pulse Oximeter Probe consists of a "Y" type probe assembly in which the Light Emitting Diode (FIG. [1] *21*, Item A) and the Photocell Detector (FIG. [1] *21*, Item B) are incorporated into modular plastic housings. Said housings have an aperture or radiation transparent window incorporated therein so that said emitter and detector may be in communication with each other when said windows are in alignment with each other. In this preferred embodiment the modular housings consist of two half shells which encapsulate each the emitter and detector, one side of said shells (FIG. [1] *21*, Items C) being fabricated of an opaque plastic material and the other half of said shells (FIG. [1] *21*, Items D) being fabricated of a radiation transparent plastic material. The housings are designed in order to accommodate at least one of a possible multiplicity of manufacturers' light emitting diodes and photocell detectors. The housings may also contain an indentation (FIG. [1] *21*, Items E) into which a locking lever of the receptacles of the disposable bandage apparatus or reusable finger attachment device may lodge in order to secure the probe housings to the receptacles of the preferred attachment device. The cable (FIG. [1] *21*, Item F) and the connector (FIG. [1] *21*, Item G) of the probe may also be interchanged in order to be compatible with a multiplicity of different manufacturers' oximeters.

[DESCRIPTION OF THE DISPOSABLE BANDAGE APPARATUS]

*Description of a Disposable Bandage Apparatus*

[The] *According to one embodiment, the* disposable bandage apparatus consists of at least one adhesive bandage strip (FIG. [2] *22*, Item A) wherein at least two receptacles (FIG. [2] *22*, Items B) are mounted on said strip. Said receptacles are mounted over apertures in the strip (FIG. [2] *22*, Items C) so that these apertures may diametrically oppose each other when the bandage strip is wrapped over the end of a patient's appendage. The Receptacles of the Disposable Bandage Apparatus may also incorporate locking levers (FIG. [2] *22*, Items D) that are intended to engage the indentations in the housings of the probe (FIG. [1] *21*, Items E) thus securing the probe housings within the bandage receptacles. The apparatus may also contain a radiation transparent window (FIG. [2] *22*, Items E) for isolation of the probe housings from the patient and may also incorporate an additional foam strip (FIG. [2] *22*, Item F) with apertures (FIG. [2] *22*, Items G) for cushioning the patient's appendage from the radiation transparent windows. FIG. [3] *23* illustrates the disposable bandage apparatus with an engaged probe as it would appear in use on a human appendage.

[DESCRIPTION OF THE REUSABLE FINGER ATTACHMENT DEVICE]

*Description of a Reusable Finger Attachment Device*

[The] *One* preferred embodiment of the Reusable Finger Attachment Device comprises a flexible plastic or foam strip (FIG. [4] *24*, Item A) with two receptacles (FIG. [4] *24*, Items B) mounted thereon. Said receptacles are mounted over apertures in the strip (FIG. [4] *24*, Items C) so that these apertures may diametrically oppose each other when the bandage strip is wrapped over the end of a patient's appendage. The strip also incorporates two perforated tabs (FIG. [4] *24*, Items D) and two additional tabs with molded knobs (FIG. [4] *24*, Items E) so that when the strip is looped over a human digit, the tabs with the perforations overlay the tabs with the knobs and these, when pressed together, can adjustably and removably interlock with each other for securing the device to a human digit. The Receptacles of the Reusable Finger Attachment Device may also incorporate locking levers (FIG. [4] *24*, Items F) that are intended to engage the indentations in the housings of the probe (FIG. [1] *21*, Items E) thus securing the probe housings within the bandage receptacles. FIG. [5] *25* illustrates the device as it would appear in use on a patient with the probe housings engaged in the Reusable Finger Attachment Device.

Other Fastening Means

As can be appreciated there are many means of fabricating [either] the Disposable Bandage Apparatus and *the* Reusable Finger Attachment Device using modular receptacles into which a universal modular probe housing could be lockingly engaged. While these devices may offer the most efficient method fabrication and/or user friendliness, they are by no means exhaustive.

Method of Use

Whether using the Disposable Bandage Apparatus or the Reusable Finger Attachment Device, the methods of use are essentially the same. With either apparatus, the end of the human appendage is wrapped by the device and, in the case of the Disposable Bandage Apparatus, the adhesive strip simply sticks to the skin of the patient. With the Reusable Finger Attachment Device, the tabs containing the perforations and knobs are simply overlaid and pushed together thus securing the device to the digit. With either device the probe housings are pushed into the receptacles of the device and are locked into place by the locking levers that engage the indentations in the probe housings. When the monitoring of the patient is complete, the locking levers of the receptacles of either device are lifted in order to release the probe housings and the probe is removed from the device. In the event that a Disposable Bandage Apparatus is in use, it is then thrown away after the probe has been removed. When a Reusable Finger Attachment Device is in use, it may be removed, washed, and reused on another patient.

[ADVANTAGES OF THE PRESENT INVENTION]

*Advantages of Some Embodiments*

[1.] The standardization of probes within a hospital whereby a multiplicity of manufacturers' oximeters could utilize probes having housings of the same size for engaging either reusable or disposable attachment devices is very favorable.

[2.] Finger attachment devices on the market today are hard wired to the probes, and when breakage occurs on the finger clip, the entire probe must be repaired or thrown away. With *some embodiments of* the present invention, when breakage occurs in either the finger attachment device or the probe itself, only the broken component has to be replaced.

[3.] A big problem exists with maintaining the cleanliness of reusable finger clips because the electronics are not removable from the finger clip and the device cannot be immersed or cleaned. With *some embodiments of* the present invention, the Reusable Finger Attachment Device can be removed from the probe and cleaned or sterilized.

While the invention has been described in relation to preferred embodiments of the invention, it will be appreciated that other embodiments, adaptations and modifications of the invention will be apparent to those skilled in the art.

What is claimed is:

[1. A pulse oximeter probe system comprising a probe having at least one light emitting diode and at least one photocell detector wherein said emitter and detector are incorporated into modular plastic housings, at least one housing having an aperture or radiation transparent window aligned with said diode, and at least a second housing having an aperture or radiation transparent window aligned with said detector; a selected one of:

(a) a reusable finger attachment device having a first modular receptacle pair mounted thereon, or (b) a disposable bandage device having a second modular receptacle pair mounted thereon;

wherein respective ones of said housings can lockingly engage and disengage respective ones of said modular receptacles and transmit and receive light through the appendage of a patient when the selected one of the above devices (a) or (b) is attached to a patient and when the the respective receptacles of the attached device; and the receptacles of the disposable bandage device or the reusable finger attachment device have locking levers for lockingly engaging and disengaging said modular probe housings, respectively.]

[2. The probe system of claim 1 in which said housings have indentations for lockingly engaging and disengaging the levers of receptacles of a disposable bandage apparatus or reusable finger attachment device.]

[3. The probe system of claim 1 wherein said disposable bandage apparatus incorporates radiation transparent windows for the isolation of the probe housings from the patient.]

[4. The probe system of claim 1 in which the probe housings of probes to be used on a multiplicity of manufacturers' oximeters are adapted to be matedly engaged with a selected reusable finger attachment device or a disposable bandage apparatus having receptacles designed to mate with said probe housings.]

[5. A reusable finger attachment device for use with a pulse oximeter probe incorporating modular housings, comprising said attachment device incorporating modular receptacles for matingly engaging said modular probe housings; wherein the receptacles of the reusable finger attachment device have locking levers for lockingly engaging and disengaging said modular probe housings.]

[6. The reusable finger attachment device of claim 5 which said modular probe housings are adapted to be removed from said reusable finger attachment device in order to clean or sterilize said reusable finger attachment device.]

[7. A method of standardizing probes comprising designing probe housings to be matingly engageable with modular receptacles of a disposable bandage apparatus and a reusable finger attachment device and further constructing said probe housings to be incorporated into probes adapted to work with at least one of a multiplicity of manufacturers' oximeters.]

*8. A sensor system for sensing a physiological parameter of a patient, the system comprising:*

*a reusable probe sensor comprising a first housing element and a second housing element, wherein the first housing element comprises at least one light emitter and the second housing element comprises at least one light detector, wherein the first and second housing elements are movably coupled and configured to receive a disposable sensor shield, wherein each of the first and second housing elements comprises a modular connector for engaging respective modular connectors of a disposable sensor shield;*

*a disposable sensor shield comprising a first liner portion having a first aperture and a second liner portion having a second aperture, wherein the first and second liner portions are configured to receive an appendage, wherein the first and second apertures are configured to be aligned to allow light from the at least one light emitter to pass through the first aperture, the appendage, and the second aperture, to the at least one light detector during use, wherein the disposable sensor shield is configured to engage the reusable probe sensor, and wherein each of the first and second liner portions comprises a modular connector for engaging respective modular connectors of the first and second housing elements, wherein at least one of the modular connectors comprises a locking member.*

*9. The system of claim 8, comprising a connector configured to couple the reusable probe sensor to a pulse oximeter system.*

*10. The system of claim 8, wherein the reusable probe sensor is a clip-type sensor.*

*11. The system of claim 8, comprising a portable monitor configured to be coupled to the reusable probe sensor.*

*12. The system of claim 8, wherein the reusable probe sensor comprises a hinge portion coupling the first and second housing elements.*

*13. The system of claim 8, wherein the reusable probe sensor comprises a spring.*

*14. The system of claim 8, wherein the disposable sensor shield forms a cavity for receiving the appendage.*

*15. The system of claim 8, wherein the disposable sensor shield is configured to slidably engage the reusable probe sensor.*

*16. The system of claim 8, wherein each of the first and second liner portions comprises an adhesive.*

*17. The system of claim 8, wherein the disposable sensor shield comprises snap-on connectors.*

*18. The system of claim 8, wherein at least one of the first and second apertures comprises a window.*

*19. The system of claim 8, wherein the modular connectors of the first and second housing elements comprise slots.*

*20. The system of claim 8, wherein the modular connectors of the first and second liner portions comprise slot engaging members.*

*21. A device for use with a reusable probe sensor in a system for sensing a physiological parameter of a patient, the device comprising:*

*a disposable sensor shield comprising a first liner portion having a first aperture and a second liner portion having a second aperture, wherein the first and second liner portions are configured to receive an appendage, wherein the first and second apertures are configured to be aligned to allow light from a light emitter of a reusable probe sensor to pass through the first aperture, the appendage, and the second aperture, to a light detector of a reusable probe sensor, and wherein the disposable sensor shield is configured to be coupled to a reusable probe sensor to shield the reusable probe sensor from contact with the appendage, wherein each of the first and second liner portions comprises a modular connector for engaging respective modular connectors of the reusable probe sensor, wherein at least one of the modular connectors comprises a locking member.*

*22. The device of claim 21, comprising one or more securing features configured to interact with one or more corresponding features of the reusable probe sensor to releasably secure the disposable sensor shield with the reusable probe sensor.*

*23. The device of claim 21, wherein the disposable sensor shield forms a cavity for receiving the appendage.*

*24. The device of claim 21, wherein the disposable sensor shield is configured to slidably engage a reusable probe sensor.*

*25. The device of claim 21, wherein each of the first and second liner portions comprises an adhesive.*

*26. The device of claim 21, wherein the disposable sensor shield comprises one or more locking features selected from the group consisting of a fastener, a hook-and-loop type material, a snap-on connector, a ring, a groove, a notch, a twistable connector, a contoured portion of a receptacle, a threaded connector, a flange, a tab, an indentation and a slot.*

*27. The device of claim 21, wherein the first liner portion is attached to the second liner portion.*

*28. The device of claim 21, wherein the first liner portion is separate from the second liner portion.*

*29. The device of claim 21, wherein at least one of the first and second apertures comprises a window.*

*30. A method of preparing a system for sensing a physiological parameter of a patent, the method comprising:*

*providing a reusable probe sensor comprising a first housing element and a second housing element, wherein the first housing element comprises at least one light emitter and the second housing element comprises at least one light detector, wherein the first and second housing elements are movably coupled and configured to receive a disposable sensor shield, wherein each of the first and second housing elements comprises a modular connector for engaging respective modular connectors of a disposable sensor shield;*

*providing a disposable sensor shield comprising a first liner portion having a first aperture and a second liner portion having a second aperture, wherein the first and second liner portions are configured to receive an appendage, wherein the first and second apertures are configured to be aligned to allow light from the at least one light emitter to pass through the first aperture, the appendage, and the second aperture, to the at least one light detector during use, wherein the disposable sensor shield is configured to engage the reusable probe sensor, and wherein each of the first and second liner portions comprises a modular connector for engaging respective*

*modular connectors of the first and second housing elements, wherein at least one of the modular connectors comprises a locking member;*

*coupling the disposable sensor shield to an appendage; and*

*coupling the disposable sensor shield to the reusable probe sensor.*

*31. The method of claim 30, comprising:*

*transmitting light through the appendage; and*

*sensing a physiological parameter of the patent.*

*32. The method of claim 30, comprising:*

*uncoupling the disposable sensor shield from the reusable probe sensor; and*

*uncoupling the disposable sensor shield from the appendage.*

* * * * *